(12) United States Patent
Egilmez et al.

(10) Patent No.: US 12,109,249 B2
(45) Date of Patent: Oct. 8, 2024

(54) COMPOSITIONS AND METHODS FOR TREATING INFLAMMATION AND CANCER

(71) Applicant: UNIVERSITY OF LOUISVILLE RESEARCH FOUNDATION, INC., Louisville, KY (US)

(72) Inventors: Nejat Egilmez, Louisville, KY (US); Neal Bhutiani, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 1106 days.

(21) Appl. No.: 16/965,797

(22) PCT Filed: Jan. 29, 2019

(86) PCT No.: PCT/US2019/015525
§ 371 (c)(1),
(2) Date: Jul. 29, 2020

(87) PCT Pub. No.: WO2019/152344
PCT Pub. Date: Aug. 8, 2019

(65) Prior Publication Data
US 2021/0038692 A1    Feb. 11, 2021

Related U.S. Application Data

(60) Provisional application No. 62/623,920, filed on Jan. 30, 2018, provisional application No. 62/623,933, filed on Jan. 30, 2018.

(51) Int. Cl.
*A61K 38/20* (2006.01)
*A61P 35/00* (2006.01)
*C07K 16/24* (2006.01)
*C07K 16/28* (2006.01)
*A61K 39/00* (2006.01)

(52) U.S. Cl.
CPC ........ *A61K 38/2066* (2013.01); *A61K 38/208* (2013.01); *A61P 35/00* (2018.01); *C07K 16/244* (2013.01); *C07K 16/2818* (2013.01); *A61K 2039/507* (2013.01)

(58) Field of Classification Search
CPC ............... A61K 38/20; A61K 38/2066; A61K 2039/507; C07K 16/244; C07K 16/2818; A61P 35/00
See application file for complete search history.

(56) References Cited

U.S. PATENT DOCUMENTS

| | | |
|---|---|---|
| 2005/0281885 A1 | 12/2005 | Egilmez et al. |
| 2010/0310560 A1 | 12/2010 | Colonna et al. |
| 2016/0144014 A1 | 5/2016 | Honda et al. |
| 2017/0274073 A1 | 9/2017 | Grogan et al. |

OTHER PUBLICATIONS

Bhutiani et al.; "Combined oral cytokine therapy effectively treats colon cancer in a murine model"; American Association for Cancer Research, Jul. 2017, vol. 77, No. 13 Supplement, p. 1604, abstract.
Karim et al.; Mouse models for colorectal cancer; American Journal of Cancer Research, Jun. 20, 2013, vol. 3, No. 3, pp. 240-250.

*Primary Examiner* — Gyan Chandra

(57) ABSTRACT

Compositions and methods for the treatment of cancer and/or inflammatory diseases are provided. A combination of interleukin-10 (IL-10) and interleukin-12 (IL-12) is used to treat cancer and/or inflammatory diseases, and a combination of an anti-PD-1 antibody and an anti-IL-17 antibody is used to treat cancer.

7 Claims, 19 Drawing Sheets

Specification includes a Sequence Listing.

MHSSALLCCL VLLTGVRASP GQGTQSENSC THFPGNLPNM LRDLRDAFSR
VKTFFQMKDQ LDNLLLKESL LEDFKGYLGC QALSEMIQFY LEEVMPQAEN
QDPDIKAHVN SLGENLKTLR LRLRRCHRFL PCENKSKAVE QVKNAFNKLQ
EKGIYKAMSE FDIFINYIEA YMTMKIRN     (SEQ ID NO: 11)

Figure 11A

SP GQGTQSENSC THFPGNLPNM LRDLRDAFSR
VKTFFQMKDQ LDNLLLKESL LEDFKGYLGC QALSEMIQFY LEEVMPQAEN
QDPDIKAHVN SLGENLKTLR LRLRRCHRFL PCENKSKAVE QVKNAFNKLQ
EKGIYKAMSE FDIFINYIEA YMTMKIRN     (SEQ ID NO: 12)

Figure 11B

MPGSALLCCL LLLTGMRISR GQYSREDNNC THFPVGQSHM LLELRTAFSQ
VKTFFQTKDQ LDNILLTDSL MQDFKGYLGC QALSEMIQFY LVEVMPQAEK
HGPEIKEHLN SLGEKLKTLR MRLRRCHRFL PCENKSKAVE QVKSDFNKLQ
DQGVYKAMNE FDIFINCIEA YMMIKMKS     (SEQ ID NO: 19)

Figure 11C

SR GQYSREDNNC THFPVGQSHM LLELRTAFSQ
VKTFFQTKDQ LDNILLTDSL MQDFKGYLGC QALSEMIQFY LVEVMPQAEK
HGPEIKEHLN SLGEKLKTLR MRLRRCHRFL PCENKSKAVE QVKSDFNKLQ
DQGVYKAMNE FDIFINCIEA YMMIKMKS     (SEQ ID NO: 20)

Figure 11D

MCPARSLLLV ATLVLLDHLS LARNLPVATP DPGMFPCLHH SQNLLRAVSN

MLQKARQTLE FYPCTSEEID HEDITKDKTS TVEACLPLEL TKNESCLNSR

ETSFITNGSC LASRKTSFMM ALCLSSIYED LKMYQVEFKT MNAKLLMDPK

RQIFLDQNML AVIDELMQAL NFNSETVPQK SSLEEPDFYK TKIKLCILLH

AFRIRAVTID RVMSYLNAS (SEQ ID NO: 14)

Figure 12A

MCHQQLVISW FSLVFLASPL VAIWELKKDV YVVELDWYPD APGEMVVLTC

DTPEEDGITW TLDQSSEVLG SGKTLTIQVK EFGDAGQYTC HKGGEVLSHS

LLLLHKKEDG IWSTDILKDQ KEPKNKTFLR CEAKNYSGRF TCWWLTTIST

DLTFSVKSSR GSSDPQGVTC GAATLSAERV RGDNKEYEYS VECQEDSACP

AAEESLPIEV MVDAVHKLKY ENYTSSFFIR DIIKPDPPKN LQLKPLKNSR

QVEVSWEYPD TWSTPHSYFS LTFCVQVQGK SKREKKDRVF TDKTSATVIC

RKNASISVRA QDRYYSSSWS EWASVPCS (SEQ ID NO: 15)

Figure 12B

RNLPVATP DPGMFPCLHH SQNLLRAVSN MLQKARQTLE FYPCTSEEID
HEDITKDKTS TVEACLPLEL TKNESCLNSR ETSFITNGSC LASRKTSFMM
ALCLSSIYED LKMYQVEFKT MNAKLLMDPK RQIFLDQNML AVIDELMQAL
NFNSETVPQK SSLEEPDFYK TKIKLCILLH AFRIRAVTID RVMSYLNAS
(SEQ ID NO: 16)

Figure 13A

IWELKKDV YVVELDWYPD APGEMVVLTC DTPEEDGITW TLDQSSEVLG
SGKTLTIQVK EFGDAGQYTC HKGGEVLSHS LLLLHKKEDG IWSTDILKDQ
KEPKNKTFLR CEAKNYSGRF TCWWLTTIST DLTFSVKSSR GSSDPQGVTC
GAATLSAERV RGDNKEYEYS VECQEDSACP AAEESLPIEV MVDAVHKLKY
ENYTSSFFIR DIIKPDPPKN LQLKPLKNSR QVEVSWEYPD TWSTPHSYFS
LTFCVQVQGK SKREKKDRVF TDKTSATVIC RKNASISVRA QDRYYSSSWS
EWASVPCS (SEQ ID NO: 17)

Figure 13B

MCQSRYLLFL ATLALLNHLS LARVIPVSGP ARCLSQSRNL LKTTDDMVKT

AREKLKHYSC TAEDIDHEDI TRDQTSTLKT CLPLELHKNE SCLATRETSS

TTRGSCLPPQ KTSLMMTLCL GSIYEDLKMY QTEFQAINAA LQNHNHQQII

LDKGMLVAID ELMQSLNHNG ETLRQKPPVG EADPYRVKMK LCILLHAFST

RVVTINRVMG YLSSA   (SEQ ID NO: 18)

Figure 14A

MCPQKLTISW FAIVLLVSPL MAMWELEKDV YVVEVDWTPD APGETVNLTC

DTPEEDDITW TSDQRHGVIG SGKTLTITVK EFLDAGQYTC HKGGETLSHS

HLLLHKKENG IWSTEILKNF KNKTFLKCEA PNYSGRFTCS WLVQRNMDLK

FNIKSSSSSP DSRAVTCGMA SLSAEKVTLD QRDYEKYSVS CQEDVTCPTA

EETLPIELAL EARQQNKYEN YSTSFFIRDI IKPDPPKNLQ MKPLKNSQVE

VSWEYPDSWS TPHSYFSLKF FVRIQRKKEK MKETEEGCNQ KGAFLVEKTS

TEVQCKGGNV CVQAQDRYYN SSCSKWACVP CRVRS   (SEQ ID NO: 19)

Figure 14B

COMPOSITIONS AND METHODS FOR TREATING INFLAMMATION AND CANCER

STATEMENT OF FEDERALLY SPONSORED RESEARCH AND DEVELOPMENT

This invention was made with government support under CA100656 awarded by the United States National Institutes of Health. The United States government has certain rights in the invention.

SEQUENCE LISTING

This application includes as the Sequence Listing the complete contents of the accompanying text file "Sequence.txt", created Jan. 25, 2019, containing 65,536 bytes, hereby incorporated by reference.

BACKGROUND OF THE INVENTION

Field of the Invention

The invention generally relates to compositions and methods for the treatment of cancer and/or inflammatory diseases. In particular, the invention provides i) methods for the treatment of cancer and/or inflammatory diseases by administering a combination of interleukin-10 (IL-10) and interleukin-12 (IL-12); and ii)) methods for the treatment of cancer by administering a combination of an anti-PD-1 antibody and an anti-IL-17 antibody.

Description of Related Art

Inflammation is generally recognized as a critical component of tumor progression. Many cancers arise from sites of infection, chronic irritation and inflammation. It is now becoming clear that the tumor microenvironment, which is largely orchestrated by inflammatory cells, is an indispensable participant in the neoplastic process, fostering proliferation, survival and migration. In addition, tumor cells have co-opted some of the signaling molecules of the innate immune system, such as selectins, chemokines and their receptors for invasion, migration and metastasis.

For example, inflammatory bowel disease (IBD) is characterized by chronic inflammation of the gastrointestinal tract in genetically susceptible individuals exposed to environmental risk factors. Together, IBD is estimated to affect more than 0.4% of Europeans and North Americans, a number that is expected to increase over time. It is well recognized that patients with IBD are at an increased risk of developing colorectal cancer (CRC), primarily as a result of chronic intestinal inflammation. More recently, patients with IBD have also been shown to be at increased risk of developing extra-intestinal malignancies, thought to be a consequence of immunosuppressive therapies and an underlying inflammatory state.

IL-10 is a pluripotent immune regulatory cytokine that is critical to the maintenance of immune homeostasis in mucosal tissues. IL-10 converts immature blood monocytes to tolerogenic macrophages, has direct suppressive effects on THI7 cell activity and conversely enhances regulatory T-cell (Treg) function. Separately, numerous studies, have demonstrated that the pro-inflammatory cytokine IL-17 plays a critical role in the genesis and progression of colon cancer. To this end, the ability of an orally-administered sustained-release formulation of IL-10 has been tested to suppress IL-17-driven intestinal polyposis/colon cancer in mouse models. Those studies demonstrated that oral IL-10 could partially suppress GI tract cancer via multiple effects on pro-tumorigenic IL-17-producing immune cells and anti-tumor cytotoxic T-cells.

In addition, the ability of another cytokine, IL-12 has been tested for the treatment of colon cancer. IL-12 directly activates antitumor cytotoxic T-lymphocytes leading to tumor kill. However, oral administration of IL-12 particles resulted in exacerbation of colon tumorigenesis, demonstrating the complexities and unpredictability of immune cell interactions and their impact on cancer development.

The use of anti-PD-1 antibodies has revolutionized cancer immunotherapy by achieving objective response rates (ORR) of 15-40% in non-small cell lung cancer (NSCLC), renal cell cancer and melanoma patients with advanced stage disease that is unresponsive to standard therapy. At the same time, a significant proportion of cancer patients either fail to respond to anti-PD-I or the initial response is transient.

In particular, colorectal cancer is one type of cancer that does not respond to anti-PD-1 therapy. Similarly, greater than 70% of lung cancer patients who have had previous standard treatment fail to respond to anti-PD-1. In both of these cancers, the pro-inflammatory cytokine interleukin-17 (IL-17) has been shown to play a role in tumorigenesis and tumor progression, but this knowledge has not heretofore been successfully translated into viable anticancer treatments.

There is a pressing need in the art to develop therapies to prevent and treat inflammatory conditions such as IBD, and to prevent and treat cancers, including cancers that are known to be associated with inflammation, as well as those for which such a link has not been established.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Compositions and methods for the treatment of cancer and/or inflammatory diseases are disclosed herein.

In some aspects, compositions are administered which comprise a therapeutically effective amount of IL-10 and IL-12, either together in a single composition or separately in different compositions. Either way, the IL-10 and IL-12 are administered together as a combination therapy for the treatment of inflammation, e.g. for the treatment of inflammatory diseases or conditions such as those that cause or increase the chance of or are otherwise associated with the development of a cancer ("cancer-related inflammation"). One example of such a disease/condition is inflammatory bowel disease (IBD). Treatment of inflammation can prevent the development of cancer. Alternatively, or in addition, the IL-10/IL-12 compositions are used for the treatment of a cancer, such as a cancer that is caused by, has an increased incidence due to, or is otherwise associated with (related to) inflammation. Examples of such cancers are gastrointestinal cancers such as colon cancer. However, other types of cancers can also be treated in this manner.

In other aspects, compositions are administered which comprise an anti-PD-1 antibody plus an anti-IL-17 antibody, either together in a single composition or separately in different compositions, as a combination therapy for the treatment of cancer. Examples of cancers treated using a combination of an anti-PD-1 antibody plus an anti-IL-17 antibody include those that are typically resistant to treatment by anti-PD-1 antibody alone, including colon cancer and lung cancer, as well as cancers which have developed resistance to treatment with other chemotherapeutic agents, and/or which have developed resistance to check point inhibitors such as anti-PD-1 antibodies. However, other types of cancers can also be treated in this manner.

It is an object of this invention to provide a method of treating a disease or condition characterized by inflammation in a subject in need thereof, comprising administering to the subject a combination of IL-10 and IL-12. In some aspects, the disease or condition is selected from the group consisting of colitis, inflammatory bowel disease (IBD) and leaky gut syndrome.

Also provided is a method of treating cancer in a subject in need thereof, comprising administering to the subject a combination of IL-10 and IL-12. In some aspects, the cancer is colon or rectal cancer. In certain aspects, the colon or rectal cancer results from a hereditary polyposis syndrome. In further aspects, the hereditary polyposis syndrome is familial adenomatous polyposis (FAP), which is characterized by the development of hundreds to thousands of adenomatous polyps in the colon followed at an early age by colorectal cancer.

Also provided is a method of restoring gut barrier integrity in a subject in need thereof, comprising administering to the subject a combination of IL-10 and IL-12.

Also provided is a composition comprising IL-10 and IL-12.

The disclosure also provides a method of treating a cancer in a subject in need thereof, comprising administering to the subject an anti-IL-17 antibody in combination an anti-PD-1 antibody. In some aspects, the cancer is not responsive to treatment with the anti-PD-1 antibody alone. In further aspects, the cancer is colon cancer or lung cancer.

Also provided is a composition comprising an anti-IL-17 antibody and an anti-PD-1 antibody.

BRIEF DESCRIPTION OF THE DRAWINGS

FIG. 11A-D. Exemplary IL-10 sequences. A, unprocessed human IL-10 with the signal sequence (SEQ ID NO: 11); B, mature, processed human IL-10 without the signal sequence (SEQ ID NO: 12); C, unprocessed mouse IL-10 with the signal sequence (SEQ ID NO: 19); D, mature, processed mouse IL-10 without the signal sequence (SEQ ID NO: 20)

FIGS. 12A and B. A, exemplary unprocessed human IL-12A amino acid sequence (SEQ ID NO: 13); B, exemplary unprocessed human IL-12B amino acid sequence (SEQ ID NO: 14).

FIGS. 13A and B. A, exemplary mature human IL-12A amino acid sequence (SEQ ID NO: 15) and B, exemplary mature human IL-12B amino acid sequence (SEQ ID NO: 16).

FIGS. 14A and B. A, exemplary unprocessed mouse IL-12A amino acid sequence (SEQ ID NO: 17) and B, exemplary unprocessed mouse IL-2B amino acid sequence (SEQ ID NO: 18).

DETAILED DESCRIPTION

Figure 1A:
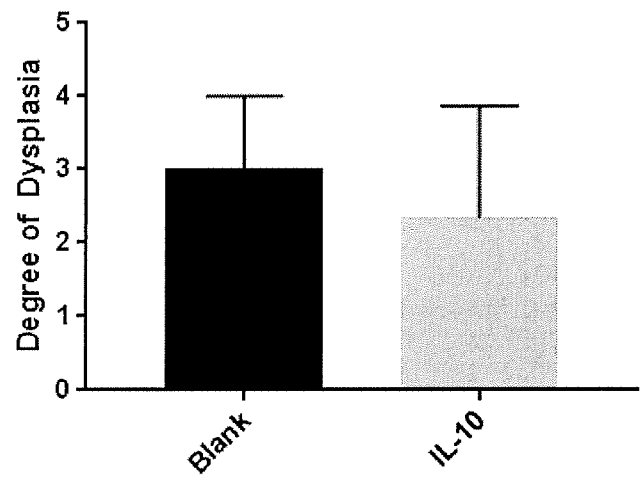
FIG. 1A-D. Oral IL-10 reduces tumor burden in mice with established disease. (A, B) Colon tumor number and maximum diameter. APC$^{min/+}$ mice were treated with oral particle-based therapy (either blank particles or particles loaded with recombinant murine IL-10) for 3 weeks beginning 4 weeks after enterotoxic B fragilis inoculation. Mice were then euthanized, and tumor number (A) and maximum tumor diameter (B) in the mouse colon were assessed. Error bars=SD, n=5 per group. (C, D) Histologic severity of disease. At the time of euthanasia, colons were fixed in 10% neutral buffered formalin, embedded in paraffin, and stained with hematoxylin and eosin as described in Methods and Materials (C). Colons were serially sectioned and degree of dysplasia classified according to the following scale: no dysplasia (0), low grade dysplasia (1), mix of low and high grade dysplasia (2), high grade dysplasia (3) and invasive cancer (4). Examples of no dysplasia (a); low grade dysplasia with pseudo-stratification of the nuclei and nuclear enlargement (b); cribriforming tumor glands significant for high grade dysplasia (c); and surface epithelium with higher grade tumor underneath significant for invasion (d) are shown. Magnification: 20× (D). Error bars=SD. n=3 per group. Significance: *, , * denote p<0.05, 0.01, 0.001, respectively.

The present disclosure provides compositions and methods for treating cancer in a subject by administering to the subject a combination of IL-10 and IL-12. Other aspects of the disclosure provide composition a subject by administering to the subject a combination of an anti-PD-1 antibody and an anti-IL-17 antibody.

Definitions

As used herein, the term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term includes antibody fragments that comprise an antigen binding domain such as Fab', Fab, F(ab')2, single domain antibodies (DABs), antibody dimers (of the same antibody or or different antibodies, such as an anti-PD-1 antibody plus and anti-IL-17 antibody), Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); DART (ds-stabilized diabody "Dual Affinity ReTargeting"); small antibody mimetics comprising one or more CDRs; a single domain antibody" (sdAb) or "VHH" such as those made by Camelid mammals and which are naturally devoid of light chains; an antibody-drug conjugate, e.g. an antibody conjugated to a cytotoxic agent such as an anti-cancer agent; etc. The antibody can be a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. The antibody may be a humanized antibody or a human antibody. A "human antibody" is one which possesses an amino acid sequence which corresponds to that of an antibody produced by a human and/or has been made using a technique for making human antibodies.

Antibodies used in the invention typically bind to their antigens with a Kd of from about 10 to 200 pM, e.g. about 10, 25, 50, 75, 100, 125, 150, 175 or 200 pM.

An "inhibitor" is a molecule which represses or prevents another molecule from engaging in a reaction.

An "antagonist" is a substance that interferes with or inhibits the physiological action of another substance or entity, such as inhibiting the physiological action of a receptor or ligand.

An "inverse agonist" is an agent that binds to the same receptor as an agonist but induces a pharmacological response opposite to that agonist.

Active Agents: IL-10 and IL-12

IL-10

Interleukin 10 (IL-10), also known as human cytokine synthesis inhibitory factor (CSIF), is an anti-inflammatory cytokine. In humans, interleukin 10 is encoded by the IL-10 gene. The IL-10 protein is a homodimer; each of its subunits is 178-amino-acids long and the subunits are bonded via a disulfide bridge. The native protein is translated with a signal peptide and is glycosylated.

An exemplary sequence of unprocessed human IL-10 (UniProtKB—P22301) which comprises an 18 amino acid signal sequence is presented in FIG. 11A (SEQ ID NO: 11) where the signal sequence is in bold and underlined. For the uses described herein, the IL-10 is usually in the form of an active disulfide-bonded homodimer that does not comprise a signal peptide (e.g. residues 19-178 of SEQ ID NO: 11), as depicted in FIG. 11B (SEQ ID NO: 12) and may or may not be glycosylated, depending on the cell line that is used to make the recombinant protein and the exact sequence of the protein, e.g. at least some human IL-10 sequences do not contain glycosylation sites, but these can be genetically engineered into the protein and most mammalian cell lines will glycosylate the protein. These sequences and variants thereof (e.g. pegylated variants) are also presented in issued U.S. Pat. No. 6,217,857, the complete contents of which is hereby incorporated by reference in entirety. Also encompassed are: orthologs of IL-10 from other species, e.g. pig, monkey, chimpanzee, etc.; and allelic variants (e.g. human allelic variants) and/or polymorphisms of IL-10; so long as they are active in the methods described herein. The mouse IL-10 sequences for unprocessed and mature forms are depicted in FIGS. 11C and 11D, respectively (SEQ ID NO: 19 and SEQ ID NO: 20).

IL-12

Interleukin 12 (IL-12) is an interleukin composed of a bundle of four alpha helices. It is a heterodimeric cytokine encoded by two separate genes: IL-12A (p35) encodes IL-12A (the alpha subunit), and IL-12B (p40) encodes IL-12 B or the beta subunit. IL-12A is translated as a 219 amino acid polypeptide in which residues 1-22 are a signal peptide. Residues 23-219 become part of the active heterodimer as subunit A. IL-12 B is translated as a 328 amino acid polypeptide in which residues 1-22 are a signal peptide and residues 23-328 become part of the active heterodimer (as subunit B). The active heterodimer (referred to as 'p70') is glycosylated and contains disulfide bonds. Exemplary sequences of the two subunits are shown in FIG. 12 A (IL-12A, UniProtKB—P29459; SEQ ID NO: 13) and FIG. 12B (IL012B, UniProtKB—P29460; SEQ ID NO: 14), where the signal sequences are underlined and in bold, and in FIG. 13A (SEQ ID NO: 15) and 13B (SEQ ID NO: 16), which show the mature forms of the A and B subunits, respectively, with signal peptides removed. Suitable IL-12 sequences and variants thereof are also described in issued U.S. Pat. No. 5,571,515, the complete contents of which is hereby incorporated by reference in entirety.

FIGS. 14A and B show the unprocessed sequences of mouse IL-12A (SEQ ID NO: 17) and IL-2B (SEQ ID NO: 18), respectively, with the signal sequences underlined and in bold. These and the processed, mature equivalents may also be employed in some aspects of the invention. Also encompassed are: orthologs of IL-12 from other species, e.g. pig, monkey, chimpanzee, gorilla, etc.; and allelic variants (e.g. human allelic variants) and/or polymorphisms of IL-12; so long as they are active in the methods described herein.

For the uses described herein, the IL-12 is usually in the form of an active disulfide-bonded heterodimer that does not comprise signal peptides. For recombinant forms of the protein, the subunits may be translated separately as unprocessed proteins which are then processed and assembled e.g. in cell culture; or may be translated separately as mature forms which assemble e.g. in cell culture or after the isolation and mixing together of each in vitro; or the mature subunits may be translated as a single fusion protein in which the subunits are linked by a linker that permits folding into an active form with proper secondary, tertiary and quaternary structure, e.g. a decapeptide containing two elastin motifs.

Various forms of recombinant and/or purified IL-10 and IL-12 are readily commercially available and/or are readily synthesized by methods known to those of skill in the art, including by synthetic "wet" chemistry or by recombinant techniques such as by cloning a suitable encoding nucleic acid sequence into an organism or cell type that can overproduce the protein. Generally, the proteins are recombinant or synthetic proteins that are produced without signal sequences.

Although exemplary sequences for IL-10 and IL-12 are shown, other variant sequences e.g. with high degrees of identity or similarity may also be used, so long as the variants are active in the present methods. For example, the variants may have sequences with at least 50, 55, 60, 65, 70, 75, 80, 85, 90, 91, 92, 93, 94, 95, 96, 97, 98 or 99% identity or similarity, as long as the function of the protein is maintained. Identity and similarity are recognized in the art as quantitative measure. To assess the similarity between two proteins, pairwise alignments are performed and pairwise alignment algorithms (BLAST, FASTA and LALIGN, etc.) are used to find the optimal alignment between two sequences including gaps. After alignment, the quantitative parameters of identity and similarity are provided for each pairwise comparison. Identity is the percentage of amino acids with a direct match in the alignment. The percent similarity of two sequences is the sum of both identical and similar matches (similar residues are residues that have undergone conservative substitution (replacement) i.e. the substituted residues are similar biochemically, structurally or functionally e.g. in charge, hydrophobicity and/or size). For example, exemplary conservative substitutions include that those occur between aliphatic residues (glycine, alanine, valine, leucine, isoleucine), hydroxyl or sulfur/selenium-containing residues (e.g. serine, cysteine, selenocysteine, threonine, methionine; aromatic residues (e.g. phenylalanine, tyrosine, tryptophan); basic residues (e.g. histidine, lysine, arginine); and acidic residues and their amides (e.g. aspartate, glutamate, asparagine, glutamine). However, substitutions need not be conservative, since some changes do not alter the function of the protein and the mutant protein would be acceptable for use as described herein. Likewise, amino- or carboxy-terminal truncated versions of the proteins, or proteins with internal deletions of e.g. about 1-5 amino acids, may also be employed, as long as the function of the protein is not compromised. In addition, amino acid sequences with modified amino or carboxyl termini are encompassed, e.g. sequences modified to prevent proteolytic degradation.

Active Agents: PD-1 Inhibitors and IL-17 Inhibitors
Anti-PD-1

Programmed cell death protein 1, also known as PD-1 and CD279 (cluster of differentiation 279), is a protein is a cell surface receptor that belongs to the immunoglobulin superfamily and is expressed on T cells and pro-B cells. PD-1 cells have a role in regulating the immune system's response to the cells of the human body by down-regulating the immune system and promoting self-tolerance by suppressing T cell inflammatory activity. This prevents autoimmune diseases, but it can also prevent the immune system from killing cancer cells.

PD-1 inhibitors activate the immune system to attack tumors and are used to treat certain types of cancer. In some aspects, the PD-1 inhibitors are anti-PD-1 antibodies. Examples of known PD-1 antibodies that may be used as described herein include but are not limited to: the monoclonal antibody pembrolizumab (KEYTRUDA®); the human IgG4 monoclonal antibody nivolumab (OPDIVO®); the monoclonal antibody cemiplimab (LIBTAYO®); MEDI0680 (AMP-514) a humanized immunoglobulin gamma 4, kappa (IgG4κ) monoclonal antibody; REGN2810 monoclonal antibody; etc. In addition, anti-PD-1 antibodies that may be used are described, for example, in issued U.S. Pat. Nos. 6,808,710; 7,488,802; 8,008,449; 8,168,757; 8,354,509; 8,779,105; 10,155,037; 10,174,113 and PCT Publication Nos. WO 2012/145493 and WO 2013/173223, the complete contents of each of which is hereby incorporated by reference in entirety.

In addition, the antigen-binding portions of the antibodies may be used in the practice of the present methods, as may be the PD-I inhibiting peptides described in U.S. Pat. No. 10,098,950, the complete contents of which is hereby incorporated by reference in entirety.

Alternative PD-1 inhibitors (e.g. antagonists, or possibly inverse agonists) that are not antibodies includes but are not limited to those various peptidomimetic compounds, macrocyclic and heterocyclic derivatives, etc.; the peptides disclosed in US patent application 2018033944; various peptide mimetics of PD-LI and PD-L2 that bind PD-I but do not activate PD-1; the anti-PD-1 fusion protein AMP-22s (a recombinant B7-DC Fc-fusion protein composed of the extracellular domain of the PD-1 ligand programmed cell death ligand 2 (PD-L2, B7-DC) and the Fc region of human immunoglobulin (Ig) G1); etc.

These PD-1 inhibitors are generally commercially available, or can be readily synthesized with reference to the sequences disclosed in the US patents/PCT publications, or other sources readily known in the art.

IL-17

Interleukin 17 (also known as IL-17A) is a pro-inflammatory cytokine. This cytokine is produced by a group of T helper cells known as T helper 17 cells in response to their stimulation with IL-23. Biologically active IL-17 interacts with type I cell surface receptor IL-17R. After binding to the receptor, IL-17 activates several signaling cascades that, in turn, lead to the induction of chemokines. Acting as chemoattractants, these chemokines recruit the immune cells, such as monocytes and neutrophils to the site of inflammation. Activation of IL-17 signaling is often observed in the pathogenesis of various autoimmune disorders, such as psoriasis. In addition, in some aspects the targeted IL-17 is IL-17C.

In some aspects, the IL-17 inhibitors that are used in the compositions and methods disclosed herein are antibodies. Examples of suitable anti-IL-17 antibodies include but are not limited to: the fully human monoclonal IgG1κ antibody secukinumab (COSENTYX®); a humanized IgG4 antibody ixekizumab (TALTZ®); as well as those described in issued U.S. Pat. Nos. 9,676,847; 9,717,791; 9,765,140; 9,845,353; 9,850,492; 9,862,765; 9,890,219; and 10,017,568, the complete contents of each of which are hereby incorporated by reference in entirety.

Antigen binding portions of such antibodies may also be used.

Alternative IL-17 inhibitors that are not antibodies include but are not limited to: inhibitors for the transcription factor that controls IL-17 expression, RORγt, e.g. and those discussed in the review by Kopalli et al. (Recent Pat Anticancer Drug Discov. 2018 Oct. 29. doi: 10.2174/1574892813666181029142812), which include RORγt antagonists that suppress Th17 cells such as digoxin, SR1001 (which targets both RORγt and RORα), TMP778, GSK805, MRL-871, MRL-248, etc. In addition, various microRNAs are known which prevent expression of PD-1, are agents that bind to an antagonize PDL-1, the ligand of PD-1.

Anti-PD-1 and anti-IL-17 antibodies are readily commercially available and/or are readily synthesized by methods known to those of skill in the art, including by synthetic "wet" chemistry or by recombinant techniques such as by cloning a suitable encoding nucleic acid sequence into an organism or cell type that can overproduce the protein.

Compositions

In general, a pharmaceutical composition as described herein generally comprises a composition that includes a pharmaceutical carrier (e.g. a pharmaceutically-acceptable vehicle or excipient) such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

Solid formulations are also encompassed. For example, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose.

Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013;5,897,876; 5,824,638; 5,464,633; 5,422,123; and 4,839,177; and WO 98/47491, each of which is incorporated herein by reference in entirety.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories or retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt capable of use in a therapeutic application.

In particular, in some aspects, the compositions provided herein comprise IL-10 and IL-12 in a single composition. The amount of IL-10 in such compositions is generally sufficient to result in a therapeutically efficacious dose as described below.

In other aspects, the compositions provided herein comprise at least one anti-PD-1 antibody and at least one anti-IL-17 antibody in a single composition. The amount of anti-PD-1 antibody in such compositions is generally sufficient to result in a therapeutically efficacious dose, as described below.

Methods of Treatment
IL-10 and IL-12
Cancer

In some aspects, this disclosure provides methods for treating a cancer (e.g. colon cancer) and/or an inflammatory disease by administering, to a subject in need thereof, a therapeutically effective amount of a combination of IL-10 and IL-12. Examples of cancers and inflammatory disorders are listed below. The subject treated as described herein are generally mammals, typically humans, but veterinary applications of this technology are also encompassed, e.g. treatment of companion pets (cats, dogs), animals of commercial value (race horses, breeding stock, etc.), animals in zoos or preserves, especially rare animals, etc.

For the treatment of cancer, for IL-10, a therapeutically effective amount is generally in the range of from about 0.5 to 80 µg/kg per day (e.g. once per day), and preferably about 1 to 40 µg/kg per day, e.g. about 1, 5, 10, 15, 20, 25, 30, 35 or 40 µg/kg per day. The amount of IL-12 in such compositions is generally sufficient to result in a dose in the range of from about 50 to about to about 500 ng/kg/day, e.g. about 50, 75, 100, 125, 150, 175, 200, 225, 250, 300, 325, 350, 275, 400, 425, 450, 475, or 500 ng/kg/day.

For the treatment of an inflammatory disease or condition, for IL-10, a therapeutically effective amount is generally in the range of from about 1 to 20 µg/kg, e.g. about 1, 5, 10, 15 or 20 µg/kg) daily; and the amount of IL-12 that is administered is generally in the same range that is administered for cancer treatment.

Anti-PD-1 and Anti-IL-17

The disclosure provides methods of treating a cancer (e.g. colon or lung cancer) by administering, to a subject in need thereof, a therapeutically effective amount of a combination of anti-PD-1 antibodies and anti-1L-17 antibodies.

For the treatment of cancer, for an anti-PD-1 antibody, a therapeutically effective amount is e.g. for nivolumab, typically 3 mg/kg (typically a fixed dose of 240 mg every 2 weeks). However, doses of 20 to 100 mg every 3 weeks have been employed. Thus, for this anti-PD-1 antibody, which is typically administered every 2-3 weeks, doses may range from e.g. about 20 to about 250 mg, e.g. about 20, 40, 60, 80, 100, 125, 150, 175, 200, 225, or 250 mg total. The agent pembrolizumab is typically administered as a 200 mg fixed dose every 3 weeks, although doses of 150 mg (e.g. about 2 mg/kg of body weight) have been suggested. The agent cemiplimab is typically administered at a dose of about 1 mg/kg to 10 mg/kg (e.g. about 1, 2, 3, 4, 5, 6, 7, 8, 9, or 10 mg/kg), to be administered intravenously every two weeks; or as a total dose or about 350 mg as an intravenous infusion over 30 minutes every 3 weeks.

Exemplary anti-IL-17 antibodies and their associated doses are: LY2439821 (ixekizumab), from about 0.06 mg/kg to about 2.0 mg/kg intravenously in a single dose e.g. every 2 weeks; secukinumab: doses ranging from about 25-300 mg as a single dose (bolus), e.g. about 25, 50, 75, 100, 125, 150, 175, 200, 225, 250, 275 or 300 mg; AIN457: doses of 3-10 mg/kg, intravenously, as a single dose, optionally re-administered weekly for 1-5 doses; brodalumab: about 50 to about 210 mg, e.g. about 50, 100, 150 or 200 mg subcutaneously, every 2 weeks for six doses per group, or about 400-about 700 mg intravenously every 4 weeks for two doses; secukinumab: about 10 mg/kg weekly for e.g. about 4 weeks or about 25-300 mg for longer times e.g. about 16 weeks; bimekizumab: subcutaneous doses of from about 10 to 300 mg once every 4 weeks (e.g. about 10, 50, 100, 150, 200, 250 or 300 mg).

In general, as used herein, the terms "treatment" or "treating" relate to any treatment of a condition of interest (e.g. a cancer, cancer and/or an inflammatory disease), including but not limited to prophylactic treatment and therapeutic treatment. As such, the terms "treatment" or "treating" may or may not include, and are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

This amounts described herein may be administered over any prescribed course, e.g. a course of from about once every 1-14 days, on consecutive or non-consecutive days, and repeated as needed e.g. once or twice every 1-12 weeks or months, or at longer intervals, especially if the condition being treated recurs. For the treatment of cancer, administration is typically oral, intravenous or intratumoral. For lung cancer, administration may also be by inhalation. Alternatively, treatment of e.g. inflammation may be carried out indefinitely on an ongoing basis (e.g. 1-4 times per day) to insure that symptoms do not recur. For inflammation, administration is typically oral, although for skin conditions, administration may be topical.

In general, the methods described herein may be coordinated with the administration of other treatments for the same condition. For example, other types of chemotherapy (e.g. methotrexate), radiation therapy, steroids, surgery, etc. may also be administered or undertaken.

As used herein, the term "cancer" refers to all types of cancer or neoplasm or malignant tumors found in animals, including leukemias, carcinomas, melanoma, and sarcomas. By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma. 100321 Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from colon cancer and liver cancer.

As used herein, the term "inflammatory disease" is used to refer to disease caused or characterized by inflammation, which is generally characterized by increased blood flow, edema, activation of immune cells (e.g., proliferation, cytokine production, or enhanced phagocytosis), heat, redness, swelling, pain and/or loss of function in the intestine (small or large) of a subject, as defined herein. The cause of the inflammation can be due to physical damage, chemical substances, micro-organisms, tissue necrosis, cancer, or other agents or conditions. Such inflammation can include acute inflammation, chronic inflammation, and recurrent inflammation. Acute inflammation is generally of relatively short duration, and last for from about a few minutes to about one to two days, although they can last several weeks. Characteristics of acute inflammation include increased blood flow, exudation of fluid and plasma proteins (edema) and emigration of leukocytes, such as neutrophils. Chronic inflammation, generally, is of longer duration, e.g., weeks to months to years or longer, and is associated histologically with the presence of lymphocytes and macrophages and with proliferation of blood vessels and connective tissue. Recurrent inflammation is inflammation which recurs after a period of time or which has periodic episodes. Some intestinal inflammation can fall within one or more categories. In some embodiments, the inflammation is gastrointestinal inflammation, such as colitis, inflammatory bowel disease, leaky gut syndrome, colon cancer or rectal cancer. The colon, rectal or colorectal cancer may be caused by or associated with a hereditary polyposis syndrome such as familial adenomatous polyposis (FAP). FAP is characterized by the development of hundreds to thousands of adenomatous polyps in the colon followed at an early age by colorectal cancer.

In some embodiments, the compositions described herein (e.g. the combined IL-10 and IL-12 compositions) can be used for the treatment of post-engraftment morbidity in transplant patients, such as bone marrow transplant patients. For example, graft versus host disease (GvHD) and graft rejection by the host may be treated, e.g. as described herein for the treatment of inflammation.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Those of skill in the art will recognize that optimum doses and dose ranges, e.g. for combination therapies, are generally determined in the course of clinical trials and may vary depending on the gender, age, genotype, etc. of the patient, as well as on the stage or severity of the disease being treated, the presence of other co-morbidities, etc. Doses are generally determined by a skilled practitioner, e.g. a physician.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments, the compositions disclosed herein are administered orally.

Other methods of administration include but are not limited to: osmotic mini-pumps, various polymeric microspheres, administration of vectors via gene therapy to produce the desired components, e.g. plasmids, viral vectors (e.g. adenoviral vectors), genetically engineered bacterial vectors, etc. that contain nucleic acid sequences encoding one or more desired agents, etc.

Microparticles. In some aspects, the active agents described herein are encapsulated into slow-release biodegradable polymeric particles, e.g. by the Phase Inversion Nanoencapsulation (PIN) method. The PIN method has been described in multiple publications (Mathiowitz, et al. Letters to Nature 386: 410-414, 1997; Egilmez, et al. 2003. Meth. in Mol. Med., Vol. H, Diagnostic and Therapeutic Methods and Reviews, ed. Barbara Driscoll, pp. 687-696. Humana Press, Totowa, NJ). PIN methods have been patented (U.S. Pat. Nos. 6,235,224; 6,616,869, the complete contents of both of which are hereby incorporated by reference). Although it is not believed that encapsulation is necessary to achieve the beneficial effects described herein, the delivery of encapsulated agents via e.g. an oral route or by inhalation provides the advantage that the therapeutic can be targeted to a issue of interest. However, other delivery methods, especially delivery methods targeted e.g. to a particular cell or tissue type, are equally efficacious.

Regardless of the route of administration, the compositions of the presently-disclosed subject matter are typically administered in amount effective to achieve the desired response. As such, the term "effective amount" is used herein to refer to an amount of the therapeutic composition sufficient to produce a measurable biological response (e.g., a decrease in cancer cells, cells which are inflamed, and/or cells which mediate or cause inflammation, e.g. cells that are markers of excessive, abnormal or unwanted inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Generally, the amount of each agent that is administered results in a level of that agent in the subject that exceeds the level that is naturally found in the subject, e.g. in the circulatory system of the subject and/or at a targeted site of interest, e.g. at, in or on a tumor or tumor cells; at, or or in inflamed tissue, etc.

In some aspects, the active agents described herein are administered "together" or "in combination". These terms encompass administration of the agents together in a single formulation, and administration in separate formulations. If the agents are administered in separate formulations, the nature of the formulations may be the same or different (e.g. one may be designed for oral administration and another for intravenous administration or for injection directly into a targeted site of action, etc.). Different preparations may be used, for example, if the agents have different solubilities, or if one agent sensitizes the subject to permit a better response to another agent, or if one agent causes more or different side effects that must be addressed, etc. Generally, when two separate preparations are administered, they are administered in close proximity with respect to time, e.g. "at the same time" (one immediately after the other), or within a short period of time (e.g. within minutes, such as up to an hour), etc. Generally, the goal of administration is to achieve an active dose of the two (or more) agents in the circulatory system system of the patient and/or at a targeted treatment site, at the same or at least at overlapping times.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed, by Sambrook, Fritsch and Maniatis, eds., Cold Spring Harbor Laboratory Press, Chapters 16 and 17; U.S. Pat. No. 4,683,195; DNA Cloning, Volumes 1 and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

EXAMPLES

Example 1

Enhanced Gut Barrier Integrity Sensitizes Colon Cancer to Immune Therapy

In this study, we tested whether oral IL-10 would be effective in eradicating established disease either alone or in combination with IL-12, a canonical Th1 cytokine that can directly activate tumor-associated CTL. The results demonstrate potent synergy between IL-10 and IL-12, involving pleiotropic effects on immune cells and the gut epithelium, with the latter activity being critical to overall therapeutic efficacy.

Figure 1B:
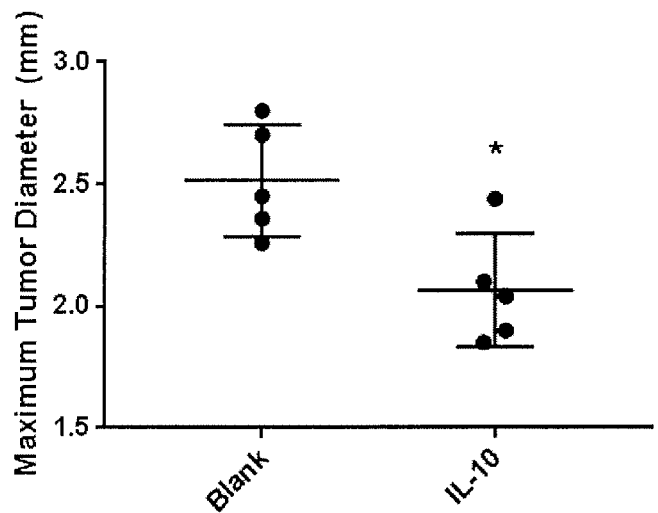
Figure 1C:
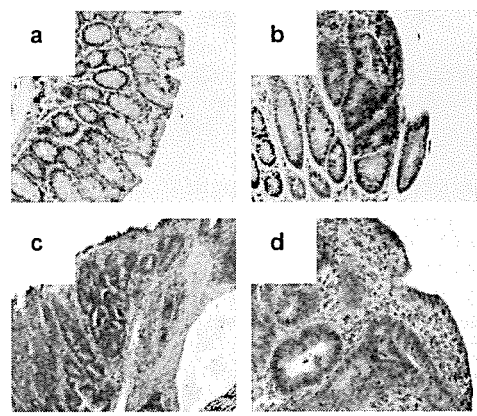
Figure 1D:
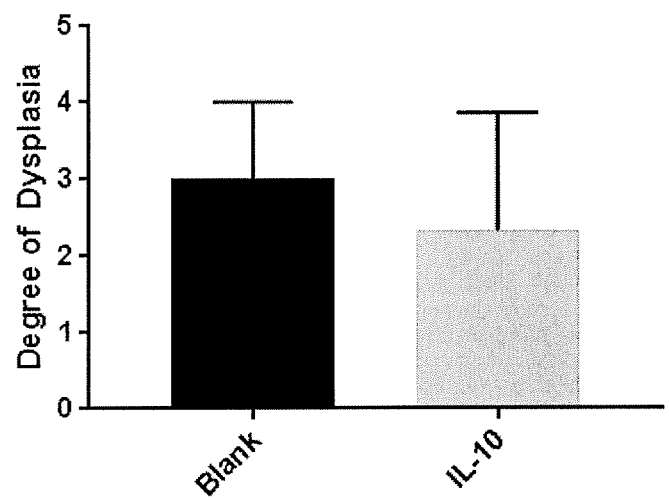

Results $APC^{min/+}$ mice were inoculated with B fragilis and were allowed to develop tumors prior to the initiation of therapy. They were then administered IL-10 for 3 weeks, and colon tumor burden as well as histologic grade were analyzed. The results demonstrate that short-term treatment reduced tumor burden by 3-fold (FIG. 1A) coupled with a modest decrease in maximum tumor diameter (FIG. 1B). In contrast, treatment did not affect tumor histopathology (FIG. 1C).

Figure 2A:
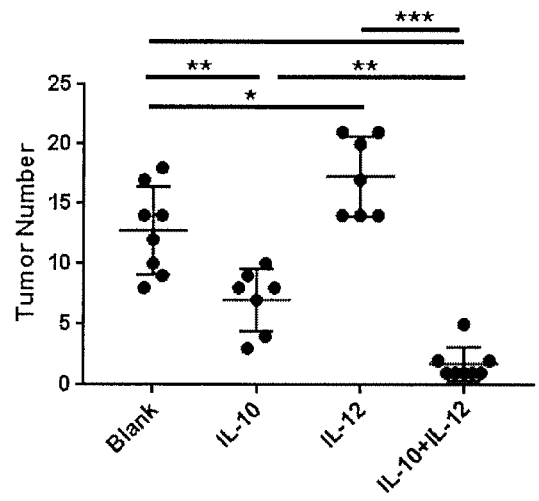
FIG. 2A-D. Oral IL-10 and IL-12 act synergistically to eradicate established disease and improve overall survival. (A, B) Colon tumor number and maximum diameter. APC$^{min/+}$/B fragilis mice were treated with oral particle-based therapy (blank, IL-10, IL-12, or a mixture of IL-10 and IL-12 particles) as in FIG. 1. Mice were then euthanized, and tumor number (A) and maximum tumor diameter (B) in the mouse colon were assessed. Error bars=SD, n=7-8 per group. (C) Histologic severity of disease. At the time of euthanasia, colons were fixed and H&E-stained sections were analyzed as in FIG. 1. Error bars=SD, n=3 per group. (D) Overall survival. APC$^{min/+}$/B fragilis mice were treated until euthanasia. n=12 and 10 for control and experimental groups, respectively. Significance: *, , * denote p<0.05, 0.01, 0.001, respectively.
Figure 2B:
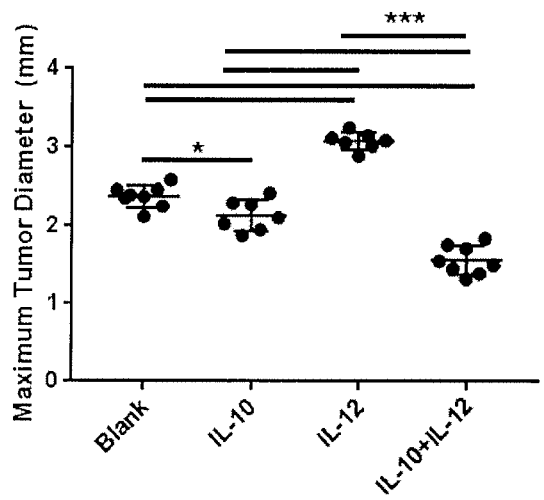

IL-10 suppresses colon tumorigenesis via its ability to reduce the prevalence of IL-17-producing T-cells with concurrent enhancement of CTL cytotoxicity. We therefore hypothesized that adding IL-12 to the treatment regimen could further augment the functional balance in favor of CTL. To test this notion, mice with established disease were treated with each cytokine separately or the two cytokines in combination. Analysis of tumor burden in mice that received monotherapy confirmed the beneficial activity of IL-10 while IL-12 increased average tumor number by approximately 30% (FIG. 2A). In contrast, combined therapy achieved near-complete tumor elimination in the majority of mice (FIG. 2A). A similar trend was observed with regard to tumor size where combination therapy mediated a significant 30% reduction in maximum tumor diameter. Importantly, and in contrast to treatment with IL-10 alone, histological analysis revealed a dramatic improvement in the pathological score of tumors in mice that received combination therapy (FIG. 2B).

Figure 2C:
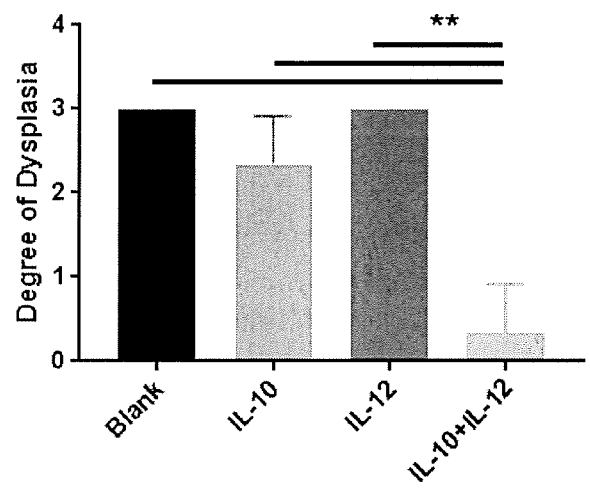
Figure 2D:
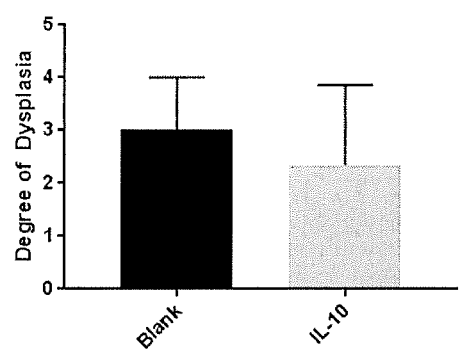

The above findings suggested that combined therapy not only arrested tumor growth but actively promoted eradication of established disease. To determine whether IL-10+IL-12 therapy could provide long-term benefit in this aggressive carcinoma model, mice with established tumors were treated continuously in a survival study. The data shown in FIG. 2C demonstrate a 30% increase in median survival in the treatment (93 days) vs the control (71 days) group. Importantly, approximately 30% of the experimental mice remained alive up to and beyond 140 days post-initiation of treatment (210 days of age), exceeding the maximum lifespan of the APC$^{min/+}$ mouse.

Figure 3A:
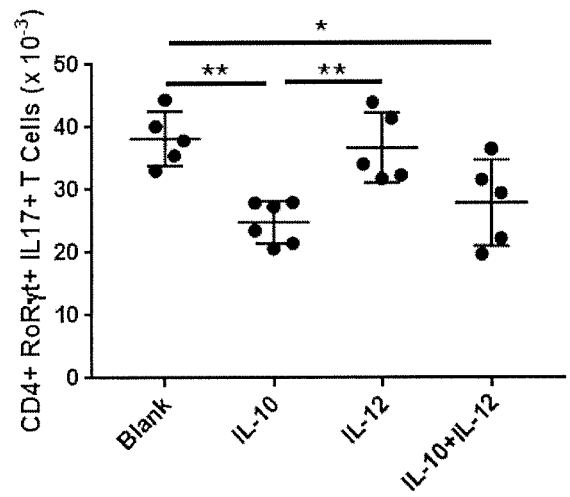
FIG. 3A-C. Distinct immunological effects of IL-10 and IL-12 on T-cell subsets are partially responsible for the antitumor synergy. (A) Effect of orally administered IL-10 and IL-12 on Th17 and CD8+ T cells. APC$^{min/+}$/B fragilis mice were treated with oral particle-based therapy (blank, IL-10, IL-12, or a mixture of IL-10 and IL-12 particles) as in FIG. 1. Mice were euthanized and lymphocytes were isolated from mesenteric lymph nodes. CD4+RORγt+ cells were gated on and analyzed for IL-17 production (Th17), and CD8+ T cells were analyzed for IFNγ production (CD8+ T-cells) by FACS. Cell numbers shown are per MLN. For CD8+ T-cell panel: filled-in circles=% of total lymphocytes; box plot=number of CD8+IFNγ+ cells. Boxes have lines at the median plus lower and upper quartiles, with whiskers extending to show the remaining data. Error bars=SD, n=5 per group. (B) and (C) Effect of CD8+ T cell depletion on tumor burden. Tumor-bearing APC$^{min/+}$ mice were treated as in FIG. 2 in the absence or presence of anti-CD8α monoclonal antibody administration and assessed for tumor burden. (B)=% CD8+ T cells; (C) tumor number. Error bars=SD, n=5-6 per group. Significance: *, ** denote p<0.05, 0.01, respectively.

Next, we wanted to delineate the cellular mechanism(s) that were responsible for the synergy. Quantitative as well as qualitative analyses of MLN T-cell populations were performed in control vs. treatment groups. Analysis of the IL-10 alone group demonstrated a 35% reduction in the number of CD4+RORγt+IL-17+Th17 cells with no significant impact on CD8+ T-cell activity (FIG. 3A). IL-12 monotherapy did not have a detectable effect on Th17 cell numbers but enhanced CTL prevalence and activity. Importantly, combination therapy reduced Th17 cell numbers and increased CTL activity, enhancing the CTL to Th17 cell ratio (FIG. 3A). These data demonstrate that each cytokine modulated distinct effector mechanisms in gut-associated immune structures with minimal cross-antagonism.

Figure 3B:
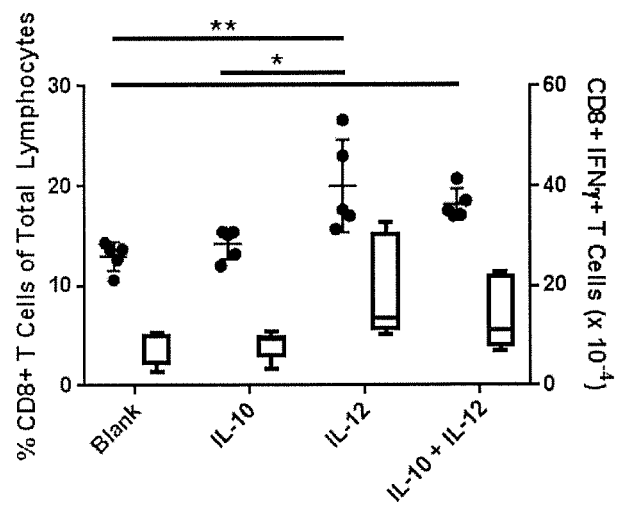
Figure 3C:
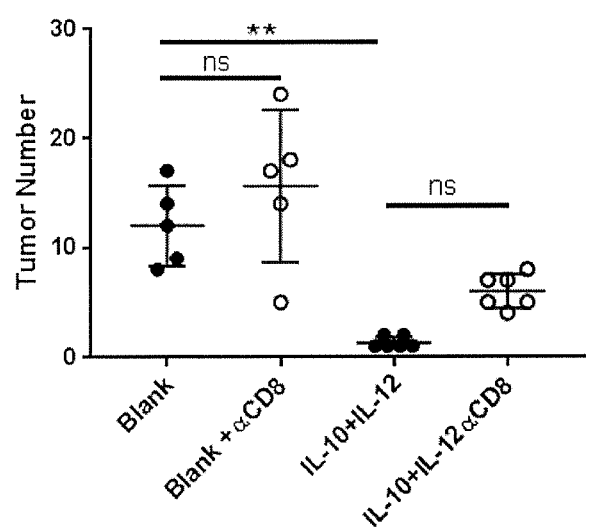

To determine whether the observed synergy between IL-10 and IL-12 was simply due to enhanced CTL activity in the presence of reduced Th17 prevalence, treatment was performed in the presence or absence of CD8+ T-cell depletion. Analysis of tumor burden revealed that depletion of CD8+ T-cells indeed resulted in reduced antitumor efficacy, though this loss was partial and did not reach statistical significance (FIG. 3B). This finding, in combination with the independent observation that IL-12 alone actually worsened disease burden, suggested additional mechanisms underpinning the observed synergy.

Figure 4A:
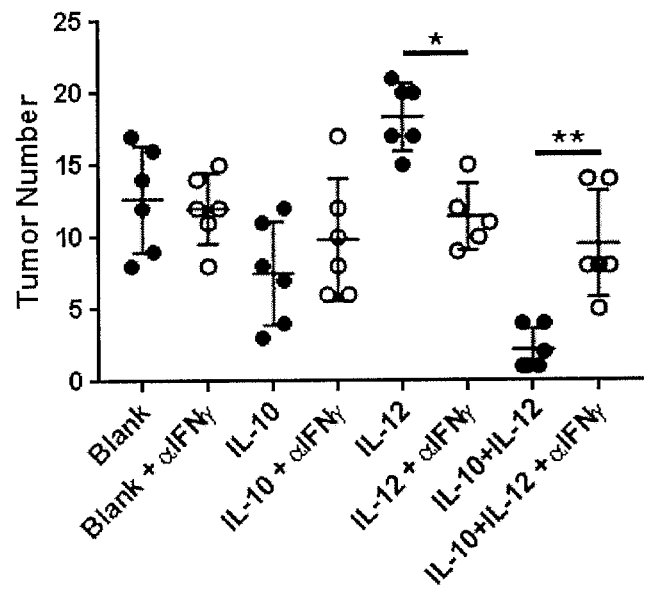
FIG. 4A-C. Therapeutic synergy requires IFNγ and is in part associated with the effects of cytokines on gut epithelial barrier integrity. (A) Effect of IFNγ neutralization on therapeutic outcome. Tumor-bearing APC$^{min/+}$ mice were treated as in FIG. 2 in the absence or presence of anti-IFNγ monoclonal antibody administration and assessed for tumor burden. (B) Gut permeability. Experimental mice were administered FITC-labeled dextran via oral gavage at the end of treatment and sera were analyzed for fluorescence to assess leakage as described in Methods and Materials. (C) Effect of IFNγ neutralization on gut permeability. Mice were treated in the absence or presence of IFNγ-neutralizing antibody and sera were analyzed as above. Naïve APC$^{min/+}$ mice served as a control for baseline permeability. Error bars=SD, n=5-6 per group for all studies. Significance: *, , * denote p<0.05, 0.01, 0.001, respectively.

IL-12 mediates its immunological activity primarily via its immediate downstream effector IFNγ. To obtain further insight into the dichotomous effects of IL-12 in our model, we first investigated the requirement for IFNγ in the pro- vs anti-tumorigenic activity of IL-12 when administered alone or in combination with IL-10, respectively. In vivo neutralization of IFNγ in the control and experimental groups demonstrated that blockade of IFNγ activity resulted in the abrogation of both the detrimental and the beneficial activities of IL-12, confirming that both pathways required IFNγ signaling (FIG. 4A). This finding suggested that in the combination therapy setting, cooperation between IFNγ and IL-10, two cytokines that are traditionally thought to be antagonistic, was responsible for the unexpected synergy.

Figure 4B:
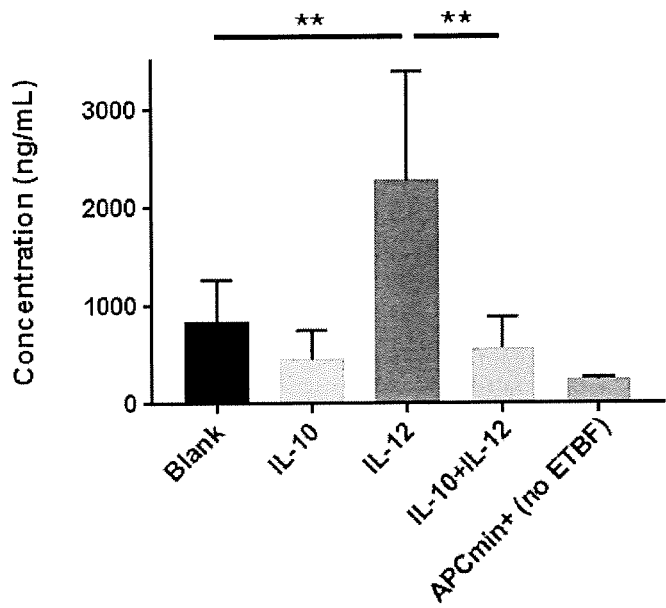
Figure 4C:
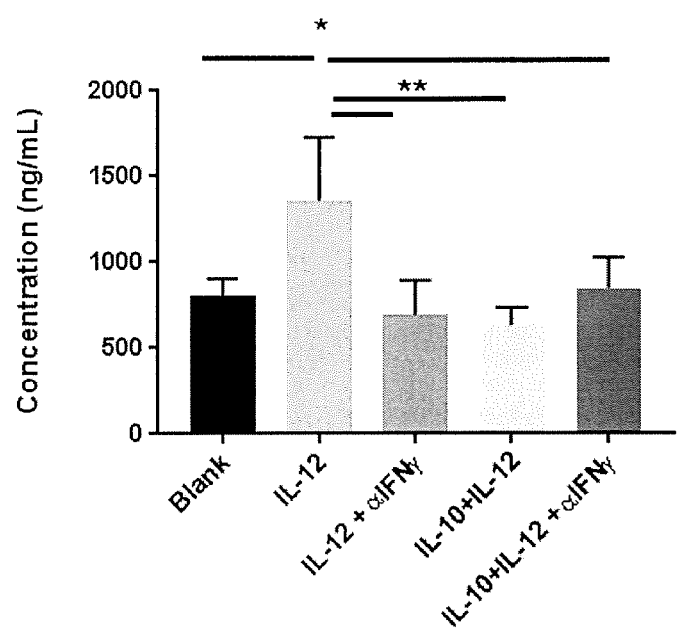

In addition to their direct effects on immune effectors, IL-10 and IFNγ are known to reciprocally modulate the paracellular physiology of gut epithelium with potential impact on pro-tumorigenic inflammatory processes. Specifically, in the APC$^{min+/-}$ model, modulation of gut permeability by DSS results in exacerbation of inflammatory activity and promotes tumorigenesis in the colon. Therefore, to determine whether the IL-10- and/or IL-12-IFNγ-epithelial barrier axis played a role in the observed synergy, we undertook examination of gut epithelial barrier function in different treatment groups. Mice were fed FITC-labeled dextran particles, and serum levels of particles were determined to assess gut permeability in each group. The data show that IL-10 slightly reduced whereas IL-12 substantially enhanced (by 3-fold) permeability compared to that in control mice (FIG. 4B). In contrast, co-administration of IL-10 with IL-12 restored serum FITC-dextran levels to steady-state, providing direct evidence that combination therapy had significant impact not only on immune cells but also on the integrity of the gut epithelium. Importantly, neutralization of IFNγ during treatment abrogated the detrimental effect of IL-12 on barrier integrity, mechanistically linking the effects of the IL-12-IFNγ axis on barrier integrity and tumor progression (FIG. 4, panels A and C).

Figure 5A:
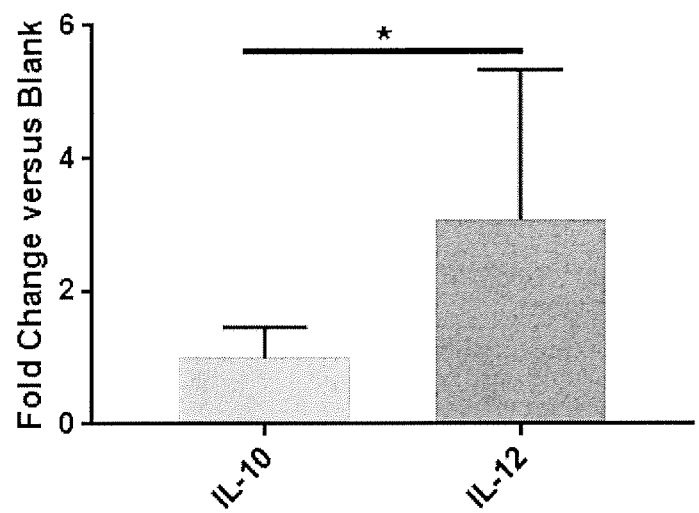
FIG. 5A-D. IL-12 induces IFNγ and IL-10RA expression in the colon. Quantitative PCR analysis of (A) IL-10RA and (B) IFNγ mRNA. Quantitative PCR was performed to evaluate relative changes in IL-10RA and IFNγ transcript levels in the colon in blank or cytokine particle-treated mice. (C) IL-10RA expression on colon epithelium. Colon sections from control (blank), IL-10, IL-12 and IL-10+IL-12-treated mice were stained for DAPI, E-cadherin, and IL-10RA and visualized by laser-scanning confocal microscopy. (D) FACS analysis of epithelial cell IL-10RA expression. Single cell preparations from colon epithelia of control and treated mice (along with a negative control, i.e. IL-10RA knockout wild-type B6 mice) were stained for EpCAM and IL-10RA expression and were analyzed by flow cytometry. Quantitative data is shown. Each circle indicates an individual mouse. Error bars=SD, n=5 per group. Significance: \*, \*\*, \*\*\* denote p<0.05, 0.01 and 0.001, respectively.
Figure 5B:
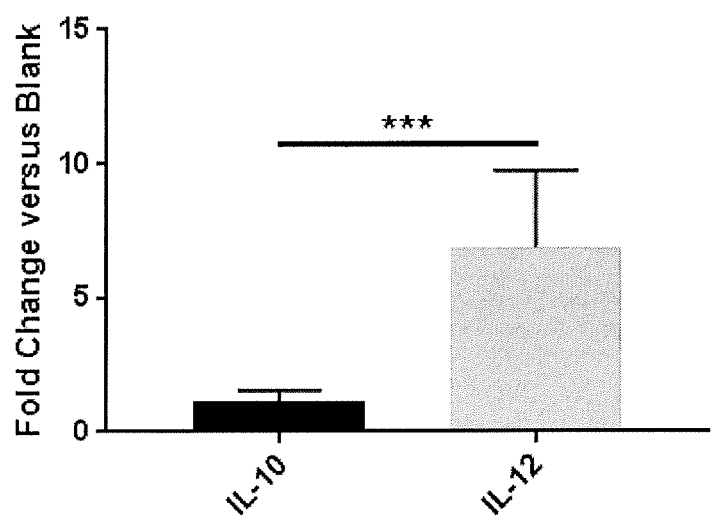
Figure 5C:
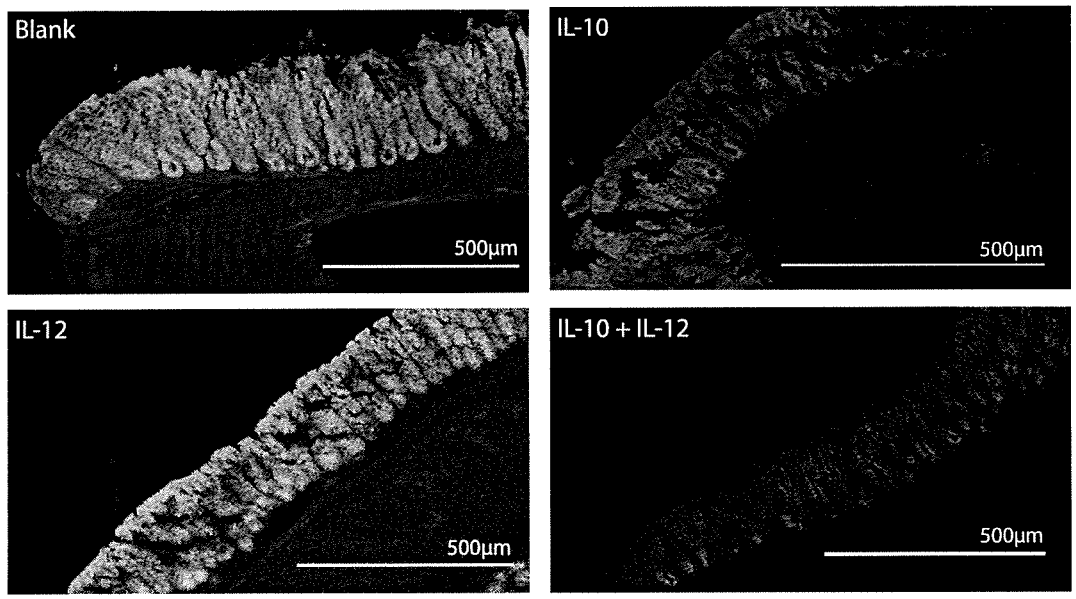
Figure 5D:
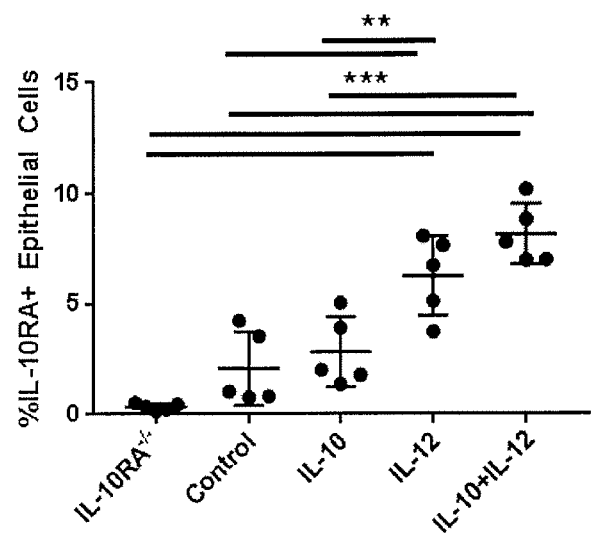

We next addressed the mechanism underlying the ability of IL-10 to restore epithelial barrier function in IL-12-treated mice. IL-10 is known to enhance tight junction protein expression in the gut epithelium. Separately, IFNγ was recently shown to induce IL-10RA expression on intestinal epithelial cells. We therefore hypothesized that sensitization of colon epithelium to IL-10 by the IFNγ-IL-10RA axis could be responsible for restoration of barrier integrity in mice receiving dual therapy. To this end, we first determined whether oral IL-12 altered IL-10RA expression in the gut. Quantitative PCR analysis revealed that IL-12 promoted 3- and 6-fold increases in IFNγ and IL-10RA mRNA expression in the colon, respectively; whereas IL-10 alone had no significant effect (FIG. 5A). To determine whether IL-10RA was upregulated on the colon epithelium, we analyzed colon tissue from control and experimental groups by confocal microscopy. The data showed robust IL-10RA expression in the colon epithelium in mice treated with IL-12 or IL-12+IL-10, whereas no significant protein could be visualized in the control or IL-10 only groups (FIG. 5B). We then quantitatively assessed IL-10RA expression on colonic epithelial cells of control vs experimental mice by FACS analysis. These data revealed an approximately 3-fold increase in IL-10RA+ epithelial cells in the colons of mice that received IL-12 particles (FIG. 5C). Collectively, these results supported the conclusion that restoration of barrier integrity in mice receiving dual treatment vs IL-12 alone was associated with increased responsiveness of IFNγ-conditioned epithelium to exogenous IL-10.

Figure 6A:
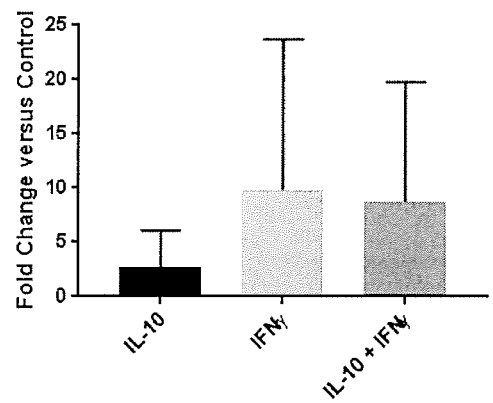
FIG. 6A-F. IFNγ and IL-10 jointly promote tight junction protein expression in the colon. Quantitative PCR analysis of (A) IL-10RA, (B) occludin and (C) claudin-4 transcripts. Colon explants were cultured for 24 hours in high glucose medium in the presence of recombinant IL-10, IFNγ, or both as described in Materials and Methods. RNA was extracted and IL-10RA, occludin and claudin-4 mRNA levels were quantified by qPCR. Error bars=SD, n=6 per group. Analysis of protein levels. Protein was extracted from colon explants cultured as above and analyzed by Western blotting to detect and quantify protein levels of (D) IL-10RA, (E) occludin and (F) claudin-4. Signal intensity of each band was normalized to β actin for loading in each lane and fold-change was calculated with respect to untreated (control) explants. Combined data from two different blots are shown. Error bars=SD, n=5-6 per group. Significance: \* denotes p<0.05.
Figure 6B:
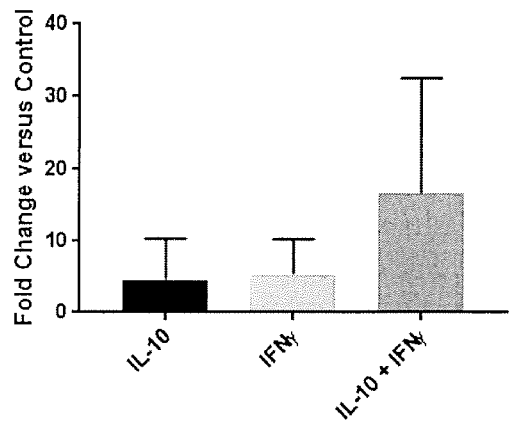
Figure 6C:
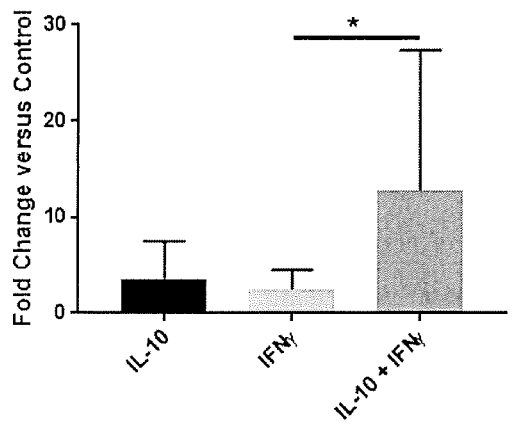
Figure 6D:
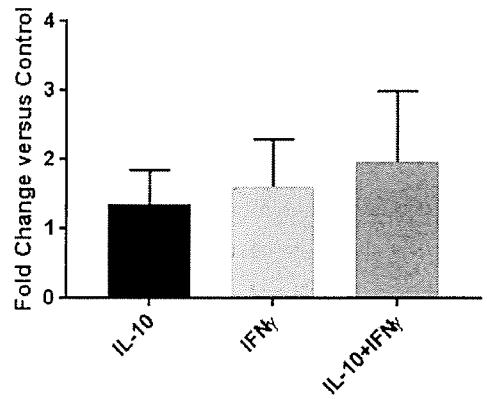
Figure 6E:
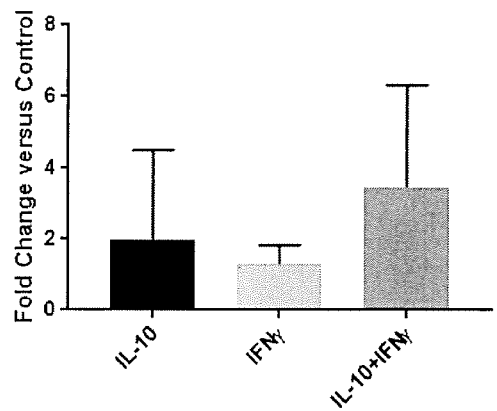
Figure 6F:
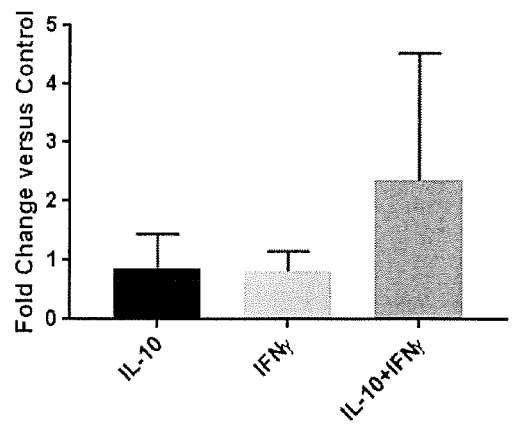

We further pursued the above studies using an in vitro colon explant culture system in which the predicted mechanism could be assessed directly. Specifically, we evaluated the effect of cytokine exposure on select tight junction protein levels. To this end, colons of B fragilis-infected APC$^{min/+}$ mice were incubated in media or media with IL-10, IFNγ or IL-10+IFNγ; and epithelial occludin, claudin-4 and IL-10RA expression were quantified by qPCR and Western blot. The results demonstrated that IFNγ, alone or in combination with IL-10, enhanced IL-10RA transcript levels by 8 to 10-fold on average (FIG. 6A). Similar increases in both occludin and claudin-4 mRNA were also observed, but only in the combination group (FIG. 6A). Western blot analysis revealed a similar trend in protein expression in explants that were exposed to IFNγ+IL-10 for all markers (FIG. 6B). Collectively, these findings further supported the mechanistic hypothesis that the stromal effect of the cytokines was associated with enhanced tight junction integrity, which required IFNγ-dependent sensitization of the epithelium to IL-10.

Discussion

Herein, we show that oral delivery of IL-10 and IL-12 can effectively eradicate established tumors in the APC$^{min/+}$/B fragilis colon cancer model. Further, we provide insight into the mechanisms that underlie the synergy between IL-10 and IL-12, two conventionally-antagonistic cytokines. Specifically, we found that, in addition to their distinct immunological effects on Th17 and CTL activity, combined administration of IL-10 and IL-12 improved gut barrier integrity via the IFNγ-IL-10RA axis, greatly enhancing the therapeutic outcome. These findings have important clinical implications for immune-based therapy of colon cancer, which has traditionally been resistant to this modality.

The primary immunological effects of IL-10 and IL-12 involved distinct activities on Th17 and CD8+ T-cell activity, respectively. Specifically, IL-10 diminished the prevalence of IL-17-producing CD4+RORγt+ Th17 cells. IL-12, on the other hand, enhanced IFNγ-producing CD8+ T-cell numbers. Importantly, these activities were independent and were not antagonistic. In addition, an unexpected finding in this study was that the sensitization of the gut epithelium to IL-10 by IL-12 was ultimately responsible for the greater part of the synergistic antitumor effect.

The above findings demonstrate that colon physiology can be effectively modulated by orally-administered slow-release cytokine formulations, establishing further proof-of-principle for the clinical potential of this therapy. This strategy provides the advantages that drugs can be delivered in a tissue-specific manner to achieve sustained physiological levels in the disease microenvironment with minimal systemic toxicity. The current data identify a novel therapeutic modality involving the synergistic use of two traditionally antagonistic cytokines.

Summary

Oral IL-10 suppressed tumor growth in the APC$^{min/+}$ mouse/*Bacteroides fragilis* colon cancer model while a similar formulation of IL-12 exacerbated disease. In contrast, combined treatment with IL-10 and IL-12 resulted in near-complete tumor eradication and a significant extension of survival. The cytokines mediated distinct immunological effects in the gut, i.e. IL-10 diminished Th17 cell prevalence whereas IL-12 induced IFNγ and enhanced CD8+ T-cell activity. Loss-of-function studies demonstrated that IL-12-driven CD8+ T-cell expansion was only partially responsible for the synergy, and that both the detrimental and the beneficial activities of IL-12 required IFNγ. Examination of colon physiology in mice receiving single vs dual treatment revealed that exacerbation of disease by IL-12 monotherapy was associated with compromised gut barrier integrity whereas combined treatment reversed this effect, uncovering additional activity by the cytokines on the stroma. Further analysis showed that the stromal effects of IL-12 included a 6-fold increase in IL-10RA expression in the colon epithelium, linking the epithelial activity of the cytokines. Finally, dual but not monotherapy induced a 3-fold increase in tight junction protein levels in the colon, identifying the mechanism by which IL-10 blocked the detrimental effect of the IL-12-IFNγ axis on barrier function without interfering with its beneficial immunological activity. These findings establish that the synergy between IL-12 and IL-10 was mediated by pleiotropic effects on the immune and the non-immune compartments and that the latter activity was critical to therapeutic outcome.

Materials and Methods

Mice and the tumor model. C57BL/6 (B6), C57BL/6J-Apc$^{Min}$/J (APC$^{Min/+}$) and B69SJL)-IL-10ra$^{tm1.1Tlg}$/J (IL-10RA knockout) mice were purchased from Jackson Laboratory. Enterotoxic *B fragilis* strain 86-5443-2-2 was a gift. For colonization with *B fragilis*, 5-6 week old APC$^{Min+}$ mice were administered clindamycin (0.1 g/L) and streptomycin (5 g/L) ad libitum in drinking water for 5 days before oral gavage (~5×10$^7$ bacteria in PBS) as previously described (Wu, et al. *Nat Med*, 15(9), pp. 1016-1022. doi:10.1038/nm.2015). All studies were conducted in accordance with guidelines set forth by the Institutional Animal Care and Use Committee at the University of Louisville (Louisville, KY).

Figure 7:
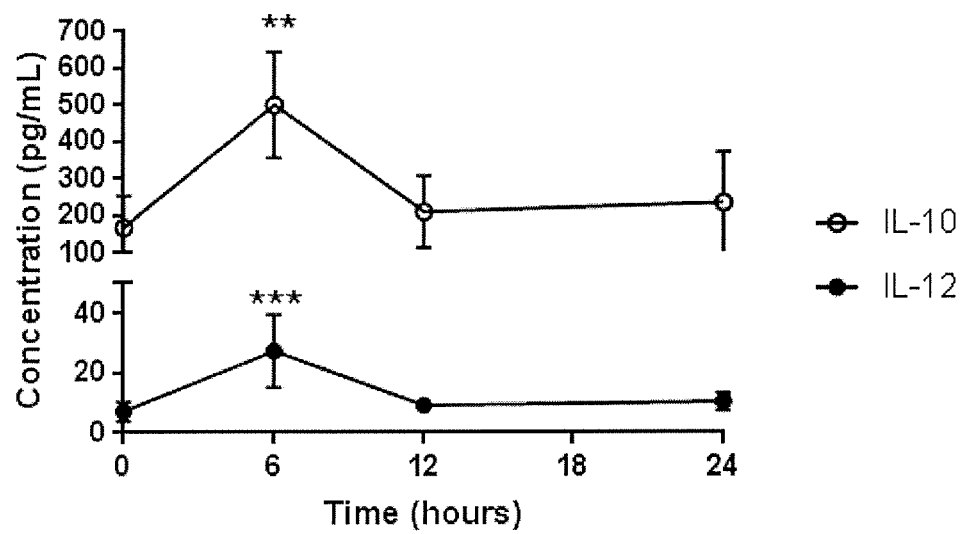
FIG. 7. Oral delivery of cytokines to gut lamina propria. Mice (C57BL/6) were administered a single dose of IL-10 and IL-12 particles (10 mg of each). Distal small bowel, cecum, and proximal colon were harvested prior to particle administration (time 0) as well as 6, 12, and 24 hours after particle administration. Tissues were flushed with ice cold PBS+P/S and placed in 1 mL 2× cell lysis buffer containing 1 mM PMSF and were homogenized followed by sonication for 20 seconds. Homogenates were then incubated on ice for 20 minutes, centrifuged for 20 minutes at 12,000×g and supernatants were analyzed for IL-10 and IL-12 by enzyme-linked immunosorbent assay (ELISA)). Error bars=SD, n=5 mice/time point. Statistical significance: \*\* and \*\*\* denote p<0.01 and 0.001, respectively.

1. Reagents and treatments. Two particle formulations were produced using a modified Phase Inversion Nanoencapsulation (PIN) process (Egilmez, et al. (2003). *Lung Cancer* (pp. 687-696): Springer): (i) control (no cytokine) and (ii) recombinant murine IL-10 or IL-12-encapsulated (Peprotech, Inc.) with a loading of 0.5 µg or 0.25 µg cytokine/mg of particles, respectively. Particles were administered via oral gavage (1 mg particles in 0.2 mL sterile water for blank, IL-10, and IL-12 treatments and 2 mL total particles in 0.2 mL sterile water for combination IL-10 and IL-12 treatment) starting 4 weeks after *B fragilis* inoculation three times per week for 3 weeks. Administration of particles resulted in a transient but significant increase in cytokine levels in the gut lamina propria (FIG. 7). For survival analysis, mice were treated until they reached the IACUC-approved euthanasia score as previously described (Chung, et al. (2014). *Cancer Res*, 74(19), pp. 5377-5385. doi: 10.1158/0008-5472.can-14-0918).

Gross intestinal preparation and tumor quantification. Colons were opened longitudinally before being fixed in 10% neutral buffered formalin. Tumor burden was quantified using a dissecting microscope.

Histology. Formalin-fixed, paraffin-embedded tissue from the distal colon was sectioned serially (5 µm sections) and subsequently stained with Hematoxylin and Eosin (H&E). Colon histology was assessed in a blinded fashion by a single tumor pathologist. Each section was classified as harboring no dysplasia, low grade dysplasia, or high grade dysplasia. Colons were then scored according to the following system based on the average severity of dysplasia in the distal colon: 0—no dysplasia; 1—low grade dysplasia only; 2—mixture of low grade and high grade dysplasia; 3—high grade dysplasia only; 4—invasive cancer.

2. Laser-scanning Confocal microscopy. Colon and tumor tissues were harvested from mice, embedded in Tissue-Plus Optimal Cutting Temperature (OCT) Compound (Fisher HealthCare, Houston, TX, USA) and snap-frozen in liquid nitrogen. Serial cryosections (25 µm) were prepared with a CRYOSTAR™ NX70, Thermo Scientific cryostat at −19° C. (Kalamazoo, MI, USA). Cryosections were kept at room temperature for at least 24 h prior to staining. A previously described immunostaining protocol was used with modifications (Egilmez, et al. (2003). *Lung Cancer* (pp. 687-696): Springer).

3. For analysis of IL-10RA expression, staining antibodies were added sequentially in the following order: IL-10RA− phycoerythrin (PE) (Novus Biologicals, Littleton, CO), CD324 (E-Cadherin) Alexa Fluor-488 (Thermo Fisher, Waltham, MA). Sections were then washed twice with 1× PBS-T and processed for imaging. For analysis of colon sections, staining antibodies were added sequentially in the following order: IL-10RA− phycoerythrin (PE) (Novus Biologicals, Littleton, CO), CD324 (E-Cadherin) ALEXA FLUOR® 488 (Thermo Fisher, Waltham, MA). Antibodies were diluted with 2% fetal calf serum (FCS) in 1× PBS pH 7.4 to 1:25 for IL-10RA-PE, and 1:25 for CD324 (E-Cadherin) ALEXA FLUOR® 488. Each antibody was sequentially incubated at 37° C. for 40 mins. Sections were washed twice with 1× PBS-T and Prolong Gold anti-fade reagent (Thermo Fisher, Waltham, MA) was added to the slides prior to imaging. Images were captured using a Leica SP5 confocal laser scanning microscope (Leica, Wetzlar, Germany) and processed using Fiji Software (Egilmez, et al. (2003). *Lung Cancer* (pp. 687-696): Springer). Panels containing confocal images were generated using Adobe Photoshop version 13.0×32. Images were marked using the drawing tools to highlight the results and to provide orientation of the tissues.

Colon epithelial cell isolation. Mouse (C57BL/6) colons were excised, flushed with PBS+penicillin and streptomycin (P/S), hemisected longitudinally, and rinsed with ice cold PBS+P/S. Colons were then cut into 5 mm pieces and placed in a 50 mL conical tube containing 20 mL HBSS+1 mM DTT+1 mM EDTA+5% FBS. Tubes were placed in a hybridization oven and incubated at 200 RPM, 37° C. for 40 minutes. Contents were then passed through a 100 µm filter and centrifuged at 1500 RPM for 5 minutes. Supernatant was discarded, and the pellet was subjected to density dependent centrifugation using a 25%-40% discontinuous Percoll gradient. Cells were harvested at the interface of the solutions and placed in 2 mL 100% FBS. Cells were centrifuged again at 1500 RPM for 5 minutes and reconstituted in 2 mL PBS+0.1% BSA for FACS analysis.

Flow cytometry. Membrane and intracellular staining of MLN or epithelial cells were performed as described (Emmerich, et al. (2012). Cancer Res, 72(14), pp. 3570-3581. doi:10.1158/0008-5472.can-12-0721). The following antibodies were used: CD4 (GK1.5, BioLegend), CD8α (53-6.7, BD Biosciences), CD16/CD32 (93, BioLegend), IL-17A (TC11-18H10.1, BioLegend), RORγt (Q31-378, BD Biosciences), IFNγ (XMG1.2, BD Biosciences), IL-10RA (1B1.3a, BioLegend), and Ep-CAM (G8.8, BioLegend).

Lymphocyte depletion and functional blockade studies. Anti-mouse CD8α (53-6.72, BioXCell) was given intraperitoneally (ip) to $APC^{min/+}$ mice (0.2 mg, three times per week for 3 weeks) to deplete CD8+ T lymphocytes. Anti-mouse IFNγ (XMG1.2, BioXCell) was injected ip (0.2 mg, three times per week for 3 weeks). All treatments were initiated on treatment day −1 (the day before receiving their first oral immunotherapy treatment) and again on treatment day 0 (the day of their first oral immunotherapy treatment). Mice were subsequently treated IP twice weekly for the duration of their 3 week oral immunotherapy treatment regimen.

Colon permeability study. Colon permeability was assessed using a FITC-dextran assay as previously described (Egilmez, et al. (2003). Lung Cancer (pp. 687-696): Springer). Briefly, $APC^{min/+}$/B fragilis mice were treated with oral immunotherapy as described above. After 3 weeks of treatment, they were water starved overnight before being gavaged with 44 mg/100 g body weight of FITC labeled dextran (FD4, Millipore Sigma, St. Louis, Missouri, USA) suspended in sterile PBS at a concentration of 100 mg/mL. After a period of 4 hours, 300 mL of blood was extracted retro-orbitally and placed in a BD SST collection tube (BD, Franklin Lakes, New Jersey, USA). After centrifugation, serum was aspirated and diluted 1:1 with sterile PBS. Samples were pipetted into a 96-well plate and analyzed using a plate reader (em: 485 nm, ex: 526 nm). Concentration of FITC-dextran was calculated based upon a standard curve.

Colon explant culture. Colon tissue pieces (0.5-1 cm length) from $APC^{min+}$/B fragilis mice were cultured in triplicates for 24 hours in complete DMEM-high glucose medium (supplemented with 10% fetal bovine serum, 1× penicillin-streptomycin solution) in a humidified atmosphere (37° C., 5% $CO_2$) in the presence of recombinant murine IL-10 (30 ng/mL, PeproTech, Rocky Hill, New Jersey, USA), recombinant murine IFNγ (20 ng/mL, PeproTech, Rocky Hill, New Jersey, USA), or a combination of recombinant murine IL-10 and IFNγ. The tissues were processed for protein preparation (tissue lysates with RIPA buffer) using a sonic dismembrator (Model 550, Fisher Scientific). These tissue lysates were used to determine the expression of IL-10RA, claudin-4, and occludin.

Western blots. Total protein lysates were collected either from colon tissue or colon epithelial cells as described above using radioimmunoprecipitation assay (RIPA) buffer (Millipore Sigma, St. Louis, Missouri, USA) and quantified using BCA protein quantification kit (Thermo Fisher Scientific, Waltham, Massachusetts, USA) per instructional manual. Total protein (20-50 µg) of was resolved on MINI-PROTEAN® TGX™ 4-20% gels (Bio-Rad, Hercules, California, USA) and transferred to polyvinylidene difluoride membrane (0.22 µm pore; Novex, Carlsbad, California, USA). After blocking with 3% (w/v) bovine serum albumin (BSA) (containing 1× TBS) for 1 h, the membrane was then incubated with HRP-conjugated anti-claudin-4, anti-occludin, anti-IL-10RA and anti-β-actin antibodies (1:500, 1:500, 1:300 and 1:20,000 dilution, respectively) at 4° C. overnight. For all proteins, chemiluminescent substrate (SUPERSIGNAL™ West Femto Maximum Sensitivity Substrate, THERMO SCIENTIFIC™, Rockford, Illinois, USA) was used to detect the protein bands (ImageQuant LAS 4000). Densitometry analysis of bands was done using ImageJ software. Antibodies for claudin-4, occludin and β-actin were purchased from Santa Cruz Biotechnologies (USA). The antibody for IL-10RA was purchased from Novus Biologicals (USA).

Quantitative PCR. Steady-state mRNA levels in colon tissue were detected with SYBR™ Green PCR Master Mix (Applied Biosystems) using the Mx3000p qPCR system (Agilent Technologies). Results were normalized to β-actin expression. The expression level was scaled using the $2^{-\Delta\Delta CT}$ method, with the average levels obtained for colons of $APC^{min/+}$/B fragilis mice treated with blank (control) microparticles set arbitrarily to 1. Primer sequences utilized were:

```
β-actin
forward
                                         (SEQ ID NO: 1)
5'-TCACCCACACTGGCCCATCTACGA-3', reverse
                                         (SEQ ID NO: 2)
5'-TGGTGAAGCTGTAGCCACGCT-3';

IL-10RA
forward
                                         (SEQ ID NO: 3)
5'-GCCAAGCCCTTCCTATGTGT-3', reverse
                                         (SEQ ID NO: 4)
5'-CCAGGGTGAACGTTGTGAGA-3';

IFNγ
forward
                                         (SEQ ID NO: 5)
5'-GGCACAGTCATTGAAAGC-3', reverse
                                         (SEQ ID NO: 6)
5'-TGCCAGTTCCTCCAGATA-3';

claudin-4
forward
                                         (SEQ ID NO: 7)
5'-ATGGCGTCTATGGGACTACA-3', reverse
                                         (SEQ ID NO: 8)
3'-TTACACATAGTTGCTGGCGG-5'
```

```
occludin
forward
                                             (SEQ ID NO: 9)
5'-CCTCCAATGGCAAAGTGAAT-3', reverse
                                             (SEQ ID NO: 10)
3'-CTCCCCACCTGTCGTGTAGT-5'.
```

Statistical Analysis. Two-tailed student's t-test was used to determine the significance of the differences between control and experimental groups in pairwise comparisons. In experiments with multiple groups homogeneity of inter-group variance was analyzed by one-way ANOVA with Tukey's honest standard difference for multiple comparisons. Log-rank test was utilized for analysis of survival studies. P values of 0.05 or less were considered statistically significant. Statistical analyses were performed using GraphPad Prism 7 (GraphPad Software, La Jolla, California, USA) and MedCalc version 17.9.7 (MedCalc Software, Ostend, Belgium).

Example 2

Anti-PD-1 and Anti-IL-17 Therapy for Lung and Colon Cancer

Anti-PD-1 and anti-IL-17 antibodies (BioXcell, Inc.) were tested in combination to determine whether IL-17 neutralization would sensitize anti-PD-1 resistant lung and colon tumors in mouse models.

Methods

Lung tumor burden determination. Lungs were harvested and trachea were cannulated with a 19 G long blunt needle and tied into place. The right lung was separated for isolation of mononuclear cells, and the left lung was infused with 10% neutral buffered formalin (Leica) for 18 hours, embedded in paraffin and sectioned serially. Nine representative sections per mouse, distributed throughout the lung, were stained with hematoxylin and eosin (H&E) and used for microscopic analysis. Images of sections were captured with the Aperio SCANSCOPE® XT Slide Scanner (Aperio Technologies, Vista, CA) system with a 20× objective. Spectrum software (Aperio) was used for quantification of lesions vs total lung area per section. Tumor burden was defined as the ratio of combined hyperplastic areas to total lung area in each section and all data from a single mouse were averaged to obtain the final percent tumor area per animal.

Results

Figure 8:
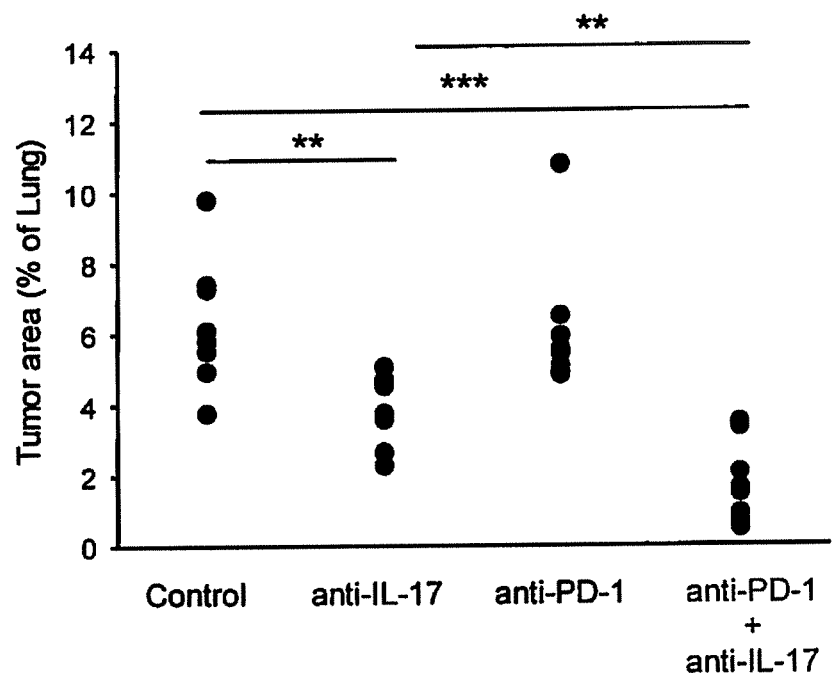
FIG. 8. IL-17 neutralization sensitized tumors to anti-PD-1 in the LSL-K-ras spontaneous lung cancer mode. Mice with established lung tumors (starting at 6 weeks post adenovirus administration) were treated with vehicle, anti-PD-1, anti-IL-17 and anti-PD-1+anti-IL-17 2×/wk for 4 weeks. Anti-PD-1 was administered by intubation-mediated intratracheal instillation encapsulated into microspheres (7 μg antibody/mg particles, 1.4 mg particles per administration). Control mice received empty particles. Anti-IL-17 was administered in soluble form (200 μg, i.p./treatment). Lung tumor burden was determined one week after the last treatment. Quantitative data were plotted with each dot representing a single mouse; n=5-8 per time point. Significance: \*\*, \*\*\* denote p values of <0.01 and 0.001.
Figure 9:
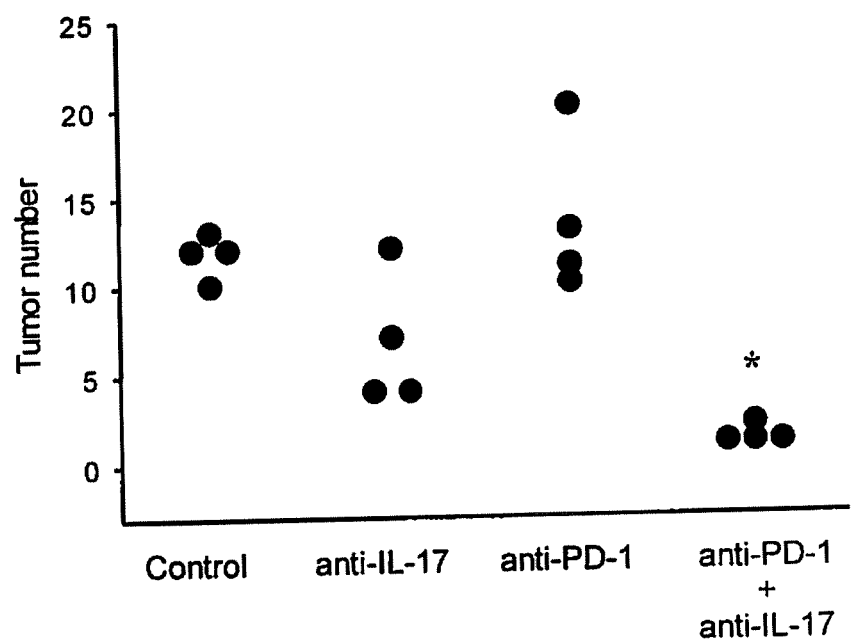
FIG. 9. IL-17 neutralization sensitized tumors to anti-PD-1 in the *Bacteroides fragilis* spontaneous colon cancer model. Mice with established colon tumors (starting 3 weeks after *B. fragilis* administration 0) were treated with control particles, anti-PD-1 particles, soluble anti-IL-17 or anti-PD-1 anti-IL-17 (same quantities and schedule as for FIG. 7 except that anti-PD-1 particles were given orally).

As shown in FIG. 8, IL-17 neutralization sensitized tumors to anti-PD-1 in the LSL-K-ras spontaneous lung cancer model. As shown in FIG. 9, IL-17 neutralization also sensitized tumors to anti-PD-1 in the *Bacteroides fragilis* spontaneous colon cancer model.

Figure 10A:
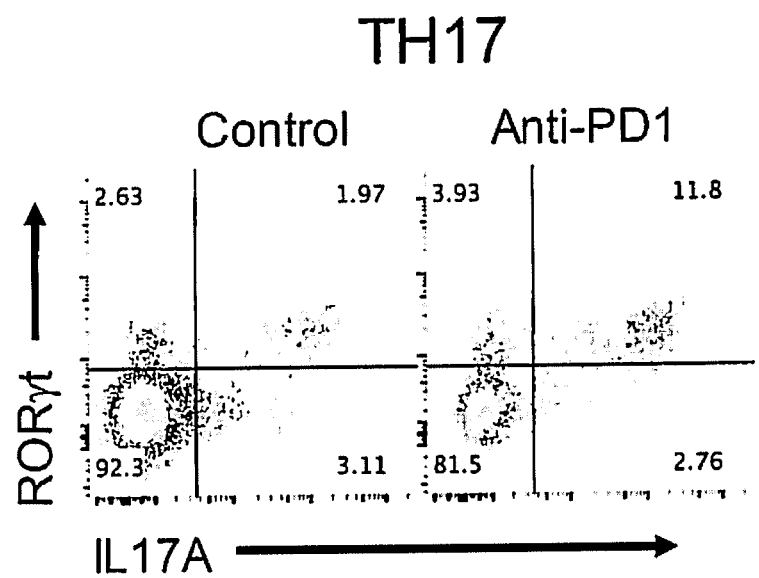
FIGS. 10A and B. Anti-PD-1 induces IL-17 production in CD4+ T-cells. Tumors were induced and treatment was administered to LSL-K-ras mice as in FIG. 8. At the end of treatment, lungs from control and anti-PD-1-treated mice were processed into single cell suspensions. CD45+CD4+ cells were gated on and analyzed for changes in RORγt (the transcription factor that drives IL-17 production) and 1L-17 expression. A, Example of flow cytometry panel from control (empty particle) and anti-PD-1 microparticle-treated mice. B, Quantitative data. Error bars=SEM, n=4/group. Significance: \*\*\* denotes p<0.001 (Student's paired t-test).
Figure 10B:
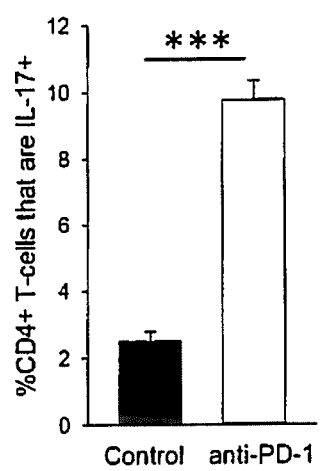

It was then tested whether anti-PD-1 treatment alone affected IL-17-producing cells. The levels of IL-17-producing CD4+ T-cells (TH17 cells) were analyzed in mice treated with anti-PD-1 compared to control mice in the LSL-K-ras lung cancer model. The results demonstrated that anti-PD-1 treatment promoted a dramatic >4-fold increase in IL-17-production by CD4+ T-cells (FIG. 10). This finding, taken together with the observations shown in FIGS. 8 and 9, demonstrate a surprising, unexpected side-effect of anti-PD-1, i.e. induction of IL-17 production, a cytokine with an established pro-tumorigenic activity. Without being bound by theory, it is believed that that side-effect counters what would otherwise be the beneficial antitumor activity of anti-PD-1 (activation of antitumor CD8+ T-cells) and is responsible for the resistance of certain cancers to anti-PD-1 therapy.

Summary

The findings demonstrated that for lung and colon cancer, anti-PD-1 alone was ineffective in achieving tumor suppression but was highly effective when co-administered with anti-IL-17.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating a cancer in a subject in need thereof, comprising
   treating the subject with an anti-PD-1 antibody,
   measuring a level of IL-17 produced by CD4+ T-cells in the subject,
   identifying an increase in IL-17 produced by CD4+ T-cells, and
   administering to the subject a combination of an anti-IL-17 antibody and an anti-PD-1 antibody,
   wherein the cancer is colon cancer or lung cancer.

2. The method of claim 1, wherein the cancer is not responsive to treatment with the anti-PD-1 antibody alone.

3. The method of claim 1, wherein the cancer is lung cancer.

4. The method of claim 1, wherein the cancer is colon cancer.

5. The method of claim 1, wherein the combination of the anti-IL-17 antibody and the anti-PD-1 antibody is administered in a singular formulation.

6. The method of claim 1, wherein the combination of the anti-IL-17 antibody and the anti-PD-1 antibody is administered in separate formulations.

7. The method of claim 1, wherein the IL-17 measured in the measuring step is IL-17A.

* * * * *

SEQUENCE LISTING

```
<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
tcacccacac tggcccatct acga                                          24

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
tggtgaagct gtagccacgc t                                             21
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gccaagccct tcctatgtgt                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ccagggtgaa cgttgtgaga                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
ggcacagtca ttgaaagc                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
tgccagttcc tccagata                                                 18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
atggcgtcta tgggactaca                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ttacacatag ttgctggcgg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 9
cctccaatgg caaagtgaat                                                                                       20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ctccccacct gtcgtgtagt                                                                                       20

<210> SEQ ID NO 11
<211> LENGTH: 178
<212> TYPE: PRT
<213> ORGANISM: Homo sapiens

<400> SEQUENCE: 11

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 12
<211> LENGTH: 160
<212> TYPE: PRT
<213> ORGANISM: Homo sapiens

<400> SEQUENCE: 12

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

<210> SEQ ID NO 13
<211> LENGTH: 219
<212> TYPE: PRT
<213> ORGANISM: Homo sapiens

<400> SEQUENCE: 13

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
        50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
                100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
        130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
            195                 200                 205

Ile Asp Arg Val Met Ser Tyr Leu Asn Ala Ser
        210                 215

<210> SEQ ID NO 14
<211> LENGTH: 328
<212> TYPE: PRT
<213> ORGANISM: Homo sapiens

<400> SEQUENCE: 14

Met Cys His Gln Gln Leu Val Ile Ser Trp Phe Ser Leu Val Phe Leu
1               5                   10                  15

-continued

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
            85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
            325

<210> SEQ ID NO 15
<211> LENGTH: 197
<212> TYPE: PRT
<213> ORGANISM: Homo sapiens

<400> SEQUENCE: 15

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
        50                  55                  60

```
Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 16
<211> LENGTH: 306
<212> TYPE: PRT
<213> ORGANISM: Homo sapiens

<400> SEQUENCE: 16

Ile Trp Glu Leu Lys Lys Asp Val Tyr Val Val Glu Leu Asp Trp Tyr
 1               5                  10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
             35                  40                  45

Ser Gly Lys Thr Leu Thr Ile Gln Val Lys Glu Phe Gly Asp Ala Gly
         50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
```

```
                    225                 230                 235                 240
Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
                290                 295                 300

Cys Ser
305

<210> SEQ ID NO 17
<211> LENGTH: 215
<212> TYPE: PRT
<213> ORGANISM: Mus musculus

<400> SEQUENCE: 17

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
                20                  25                  30

Cys Leu Ser Gln Ser Arg Asn Leu Leu Lys Thr Thr Asp Asp Met Val
                35                  40                  45

Lys Thr Ala Arg Glu Lys Leu Lys His Tyr Ser Cys Thr Ala Glu Asp
            50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
                100                 105                 110

Ser Leu Met Met Thr Leu Cys Leu Gly Ser Ile Tyr Glu Asp Leu Lys
                115                 120                 125

Met Tyr Gln Thr Glu Phe Gln Ala Ile Asn Ala Ala Leu Gln Asn His
            130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
                180                 185                 190

Ile Leu Leu His Ala Phe Ser Thr Arg Val Val Thr Ile Asn Arg Val
                195                 200                 205

Met Gly Tyr Leu Ser Ser Ala
            210                 215

<210> SEQ ID NO 18
<211> LENGTH: 335
<212> TYPE: PRT
<213> ORGANISM: Mus musculus

<400> SEQUENCE: 18

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
```

-continued

```
                  20                  25                  30
    Val Glu Val Asp Trp Thr Pro Asp Ala Pro Gly Glu Thr Val Asn Leu
                  35                  40                  45
    Thr Cys Asp Thr Pro Glu Glu Asp Ile Thr Trp Thr Ser Asp Gln
     50                  55                  60
    Arg His Gly Val Ile Gly Ser Gly Lys Thr Leu Thr Ile Thr Val Lys
     65                  70                  75                  80
    Glu Phe Leu Asp Ala Gly Gln Tyr Thr Cys His Lys Gly Gly Glu Thr
                      85                  90                  95
    Leu Ser His Ser His Leu Leu Leu His Lys Lys Glu Asn Gly Ile Trp
                 100                 105                 110
    Ser Thr Glu Ile Leu Lys Asn Phe Lys Asn Lys Thr Phe Leu Lys Cys
                 115                 120                 125
    Glu Ala Pro Asn Tyr Ser Gly Arg Phe Thr Cys Ser Trp Leu Val Gln
                 130                 135                 140
    Arg Asn Met Asp Leu Lys Phe Asn Ile Lys Ser Ser Ser Ser Ser Pro
    145                 150                 155                 160
    Asp Ser Arg Ala Val Thr Cys Gly Met Ala Ser Leu Ser Ala Glu Lys
                     165                 170                 175
    Val Thr Leu Asp Gln Arg Asp Tyr Glu Lys Tyr Ser Val Ser Cys Gln
                 180                 185                 190
    Glu Asp Val Thr Cys Pro Thr Ala Glu Thr Leu Pro Ile Glu Leu
                 195                 200                 205
    Ala Leu Glu Ala Arg Gln Gln Asn Lys Tyr Glu Asn Tyr Ser Thr Ser
                 210                 215                 220
    Phe Phe Ile Arg Asp Ile Ile Lys Pro Asp Pro Lys Asn Leu Gln
    225                 230                 235                 240
    Met Lys Pro Leu Lys Asn Ser Gln Val Glu Val Ser Trp Glu Tyr Pro
                     245                 250                 255
    Asp Ser Trp Ser Thr Pro His Ser Tyr Phe Ser Leu Lys Phe Phe Val
                 260                 265                 270
    Arg Ile Gln Arg Lys Lys Glu Lys Met Lys Glu Thr Glu Glu Gly Cys
                 275                 280                 285
    Asn Gln Lys Gly Ala Phe Leu Val Glu Lys Thr Ser Thr Glu Val Gln
                 290                 295                 300
    Cys Lys Gly Gly Asn Val Cys Val Gln Ala Gln Asp Arg Tyr Tyr Asn
    305                 310                 315                 320
    Ser Ser Cys Ser Lys Trp Ala Cys Val Pro Cys Arg Val Arg Ser
                     325                 330                 335

<210> SEQ ID NO 19
<211> LENGTH: 178
<212> TYPE: PRT
<213> ORGANISM: Mus musculus

<400> SEQUENCE: 19

Met Pro Gly Ser Ala Leu Leu Cys Cys Leu Leu Leu Leu Thr Gly Met
    1               5                   10                  15
    Arg Ile Ser Arg Gly Gln Tyr Ser Arg Glu Asp Asn Asn Cys Thr His
                     20                  25                  30
    Phe Pro Val Gly Gln Ser His Met Leu Leu Glu Leu Arg Thr Ala Phe
                 35                  40                  45
    Ser Gln Val Lys Thr Phe Phe Gln Thr Lys Asp Gln Leu Asp Asn Ile
     50                  55                  60
```

```
Leu Leu Thr Asp Ser Leu Met Gln Asp Phe Lys Gly Tyr Leu Gly Cys
 65                 70                  75                  80

Gln Ala Leu Ser Glu Met Ile Gln Phe Tyr Leu Val Glu Val Met Pro
                 85                  90                  95

Gln Ala Glu Lys His Gly Pro Glu Ile Lys Glu His Leu Asn Ser Leu
                100                 105                 110

Gly Glu Lys Leu Lys Thr Leu Arg Met Arg Leu Arg Arg Cys His Arg
            115                 120                 125

Phe Leu Pro Cys Glu Asn Lys Ser Lys Ala Val Glu Gln Val Lys Ser
        130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser

<210> SEQ ID NO 20
<211> LENGTH: 160
<212> TYPE: PRT
<213> ORGANISM: Mus musculus

<400> SEQUENCE: 20

Ser Arg Gly Gln Tyr Ser Arg Glu Asp Asn Asn Cys Thr His Phe Pro
1               5                  10                  15

Val Gly Gln Ser His Met Leu Leu Glu Leu Arg Thr Ala Phe Ser Gln
                20                  25                  30

Val Lys Thr Phe Phe Gln Thr Lys Asp Gln Leu Asp Asn Ile Leu Leu
            35                  40                  45

Thr Asp Ser Leu Met Gln Asp Phe Lys Gly Tyr Leu Gly Cys Gln Ala
        50                  55                  60

Leu Ser Glu Met Ile Gln Phe Tyr Leu Val Glu Val Met Pro Gln Ala
 65                 70                  75                  80

Glu Lys His Gly Pro Glu Ile Lys Glu His Leu Asn Ser Leu Gly Glu
                 85                 90                  95

Lys Leu Lys Thr Leu Arg Met Arg Leu Arg Arg Cys His Arg Phe Leu
                100                 105                 110

Pro Cys Glu Asn Lys Ser Lys Ala Val Glu Gln Val Lys Ser Asp Phe
            115                 120                 125

Asn Lys Leu Gln Asp Gln Gly Val Tyr Lys Ala Met Asn Glu Phe Asp
        130                 135                 140

Ile Phe Ile Asn Cys Ile Glu Ala Tyr Met Met Ile Lys Met Lys Ser
145                 150                 155                 160
```